US010588955B2

United States Patent
(12) United States Patent
Kong et al.

(10) Patent No.: US 10,588,955 B2
(45) Date of Patent: Mar. 17, 2020

(54) ***STREPTOCOCCUS PNEUMONIAE* PROTEIN ANTIGEN, AND PREPARATION METHOD AND USE THEREOF**

(71) Applicants: CHANGCHUN BCHT BIOTECHNOLOGY CO., Changchun (CN); JILIN UNIVERSITY, Changchun (CN)

(72) Inventors: Wei Kong, Changchun (CN); Yongge Wu, Changchun (CN); Jingcai Lu, Changchun (CN); Tianxu Sun, Changchun (CN); Man Xu, Changchun (CN); Dandan Wang, Changchun (CN); Hongjia Hou, Changchun (CN); Yunliang Dong, Changchun (CN)

(73) Assignees: Changchun BCHT Biotechnology Co., Changchun (CN); Jilin University, Changchun (CN)

( * ) Notice: Subject to any disclaimer, the term of this patent is extended or adjusted under 35 U.S.C. 154(b) by 94 days.

(21) Appl. No.: 15/563,459

(22) PCT Filed: Mar. 29, 2016

(86) PCT No.: PCT/CN2016/077667

§ 371 (c)(1),
(2) Date: Sep. 29, 2017

(87) PCT Pub. No.: WO2016/155605

PCT Pub. Date: Oct. 6, 2016

(65) Prior Publication Data

US 2018/0214530 A1 Aug. 2, 2018

(30) Foreign Application Priority Data

Apr. 3, 2015 (CN) .......................... 2015 1 0157541

(51) Int. Cl.

| | |
|---|---|
| ***A61K 39/085*** | (2006.01) |
| ***C07H 21/02*** | (2006.01) |
| ***A61K 39/02*** | (2006.01) |
| ***A61K 39/09*** | (2006.01) |
| ***C12N 15/62*** | (2006.01) |
| ***C07K 14/315*** | (2006.01) |
| ***C12N 15/70*** | (2006.01) |
| ***C07K 19/00*** | (2006.01) |
| ***A61K 39/39*** | (2006.01) |
| *A61K 39/00* | (2006.01) |

(52) U.S. Cl.

CPC ............ *A61K 39/092* (2013.01); *A61K 39/09* (2013.01); *A61K 39/39* (2013.01); *C07K 14/315* (2013.01); *C07K 14/3156* (2013.01); *C07K 19/00* (2013.01); *C12N 15/62* (2013.01); *C12N 15/70* (2013.01); *A61K 2039/55505* (2013.01); *C07K 2319/00* (2013.01)

(58) Field of Classification Search

CPC ........ A61K 38/02; A61K 39/00; A61K 39/02; A61K 39/09

USPC ..... 424/9.1, 9.2, 184.1, 185.1, 190.1, 192.1, 424/234.1, 237.1; 536/23.1, 23.4, 23.7

See application file for complete search history.

(56) References Cited

FOREIGN PATENT DOCUMENTS

| | | |
|---|---|---|
| CN | 104470538 A | 3/2015 |
| CN | 104844712 A | 8/2015 |
| WO | WO 2013/191591 A1 | 12/2013 |

OTHER PUBLICATIONS

Chinese First Office Action, dated Sep. 29, 2017, in Chinese Patent Application No. 201510157541.X, a related application, 15 pp (with English translation).

Chinese Second Office Action, dated Jun. 12, 2018, in Chinese Patent Application No. 201510157541.X, a related application, 10 pp (with English translation).

Oliveira et al. (2003) "Expression of *Streptococcus pneumoniae* antigens, PsaA (pneumococcal surface antigen A) and PspA (pneumococcal surface protein A) by *Lactobacillus casei*," FEMS Microbiology Letters 227:25-31.

European Search Report, dated Aug. 20, 2018, corresponding to European Application No. 16771360.1, a related application, 7 pp.

Cao et al. (Jun. 9, 2007) "Enhanced Protection Against Pneumococcal Infection Elicited by Immunization with the Combination of PspA, PspC, and ClpP," Vaccine 25(27):4996-5005.

Goulart et al. (Mar. 2013) "Characterization of Protective Immune Responses Induced by Pneumococcal Surface Protein A in Fusion with Pneumolysin Derivatives," 8(3): Article No. e59605.

Lu et al. (Jan. 1, 2015) "Protective Immune Responses Elicited by Fusion Protein Containing PsaA and PspA Fragments," Immunological Investigations GB 44(5):482-496.

Pope et al. (2015) "Genetic Conjugation of Components in Two Pneumococcal Fusion Protein Vaccines Enhances Paediatric Mucosal Immune Responses," Vaccine. 33(14):1711-1718.

Tarahomjoo, S. (2014) "Recent Approaches in Vaccine Development Against *Streptococcus pneumonia*," Journal of Molecular Microbiology and Biotechnology 24(4):215-227.

Fischer Walker et al. (Apr. 12, 2013) "Global burden of childhood pneumonia and diarrhea," Lancet. 381(9875):1405-1416.

Genbank Database [Online] (Jul. 5, 2017) "RecName: Full=Manganese ABC transporter substrate-binding lipoprotein; AltName: Full=Pneumococcal surface adhesin A; Flags: Precursor," Accession No. P0A4G2.1. National Center for Biotechnology Information. Accessible on the Internet at URL: https://www.ncbi.nlm.nih.gov/protein/P0A4G2.1. [Last Accessed Nov. 6, 2017].

Genbank Database [Online] (Oct. 2, 1998) "*Streptococcus pneumoniae* pneumococcal surface protein A PspA (pspA) gene, complete cds," Accession No. U89711.1. National Center for Biotechnology Information. Accessible on the Internet at URL: https://www.ncbi.nlm.nih.gov/nuccore/U89711.1. [Last Accessed Nov. 6, 2017].

(Continued)

*Primary Examiner* — Rodney P Swartz
(74) *Attorney, Agent, or Firm* — Leydig, Voit & Mayer, Ltd.

(57) ABSTRACT

Provided are a fusion protein of a pneumococcal surface adhesin A (PsaA) and a pneumococcal surface protein A (PspA), and preparation method and use thereof. Also provide are a nucleic acid for encoding the protein, carrier and cell for expressing the protein, and vaccine composition comprising the protein.

18 Claims, 7 Drawing Sheets

Specification includes a Sequence Listing.

(56) References Cited

OTHER PUBLICATIONS

Genbank Database [Online] (Oct. 22, 2008) "*Streptococcus pneumoniae* pneumococcal surface protein A (pspA) gene, complete cds," Accession No. M74122.1. National Center for Biotechnology Information. Accessible on the Internet at URL: https://www.ncbi.nlm.nih.gov/nuccore/M74122.1. [Last Accessed Nov. 6, 2017].

Genbank Database [Online] (Sep. 27, 2000) "*Streptococcus pneumoniae* strain EF3296 PspA (pspA) gene, partial cds," Accession No. AF071816.1. National Center for Biotechnology Information. Accessible on the Internet at URL: https://www.ncbi.nlm.nih.gov/nuccore/AF071816.1. [Last Accessed Nov. 6, 2017].

Lin et al. (2006) "肺炎球菌疫苗新策略 [New Strategy for Pneumococcal Vaccine]," 国际生物 制品学杂志 [International Journal of Biologics]. vol. 29. No. 10. 3 pgs.—provided with an English abstract.

International Search Report with Written Opinion corresponding to International Patent Application No. PCT/CN2016/077667, dated Jun. 27, 2016.

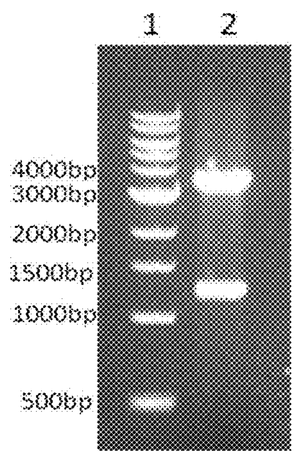
Figure 1.1
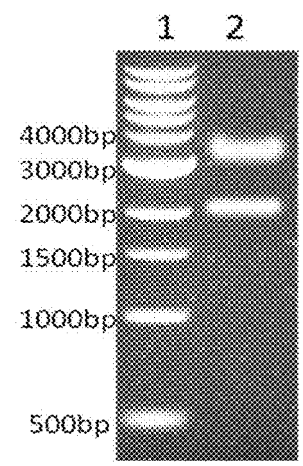
Figure 1.2
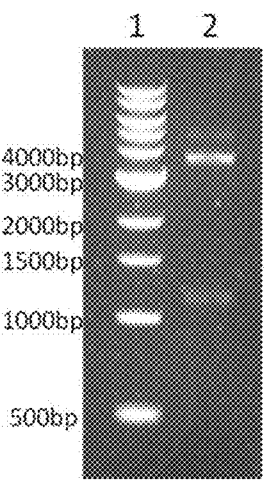
Figure 1.3

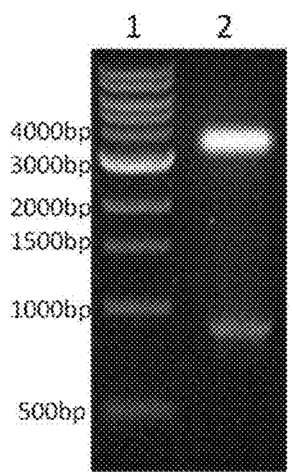
Figure 1.4
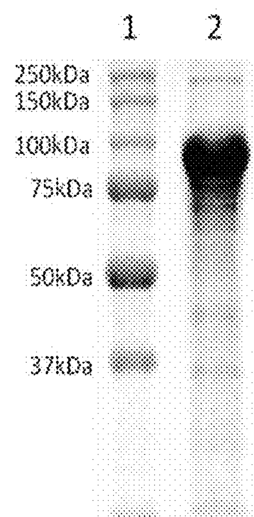
Figure 2.1
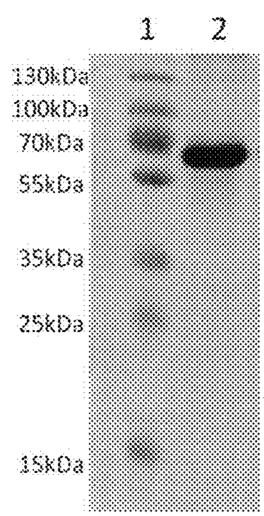
Figure 2.2

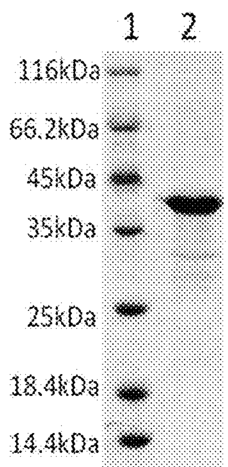
Figure 2.3
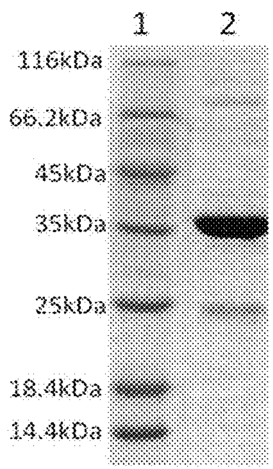
Figure 2.4
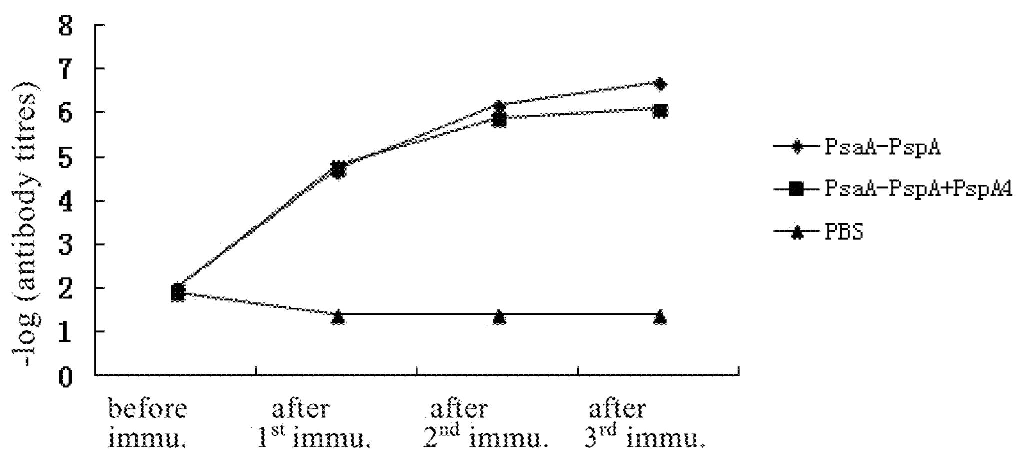
Figure 3.1

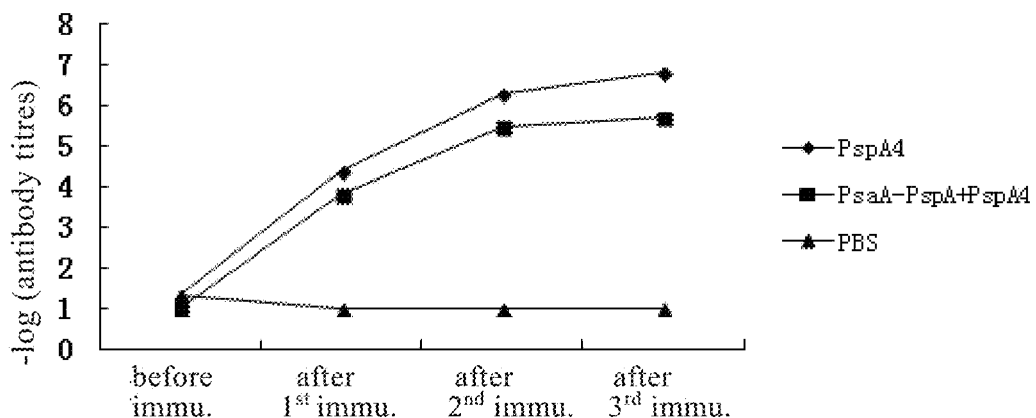
Figure 3.2
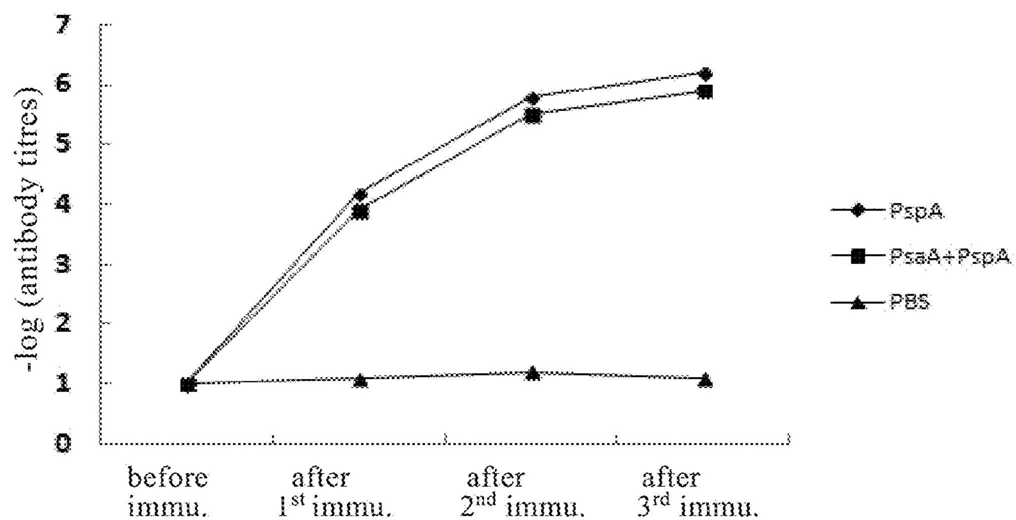
Figure 3.3
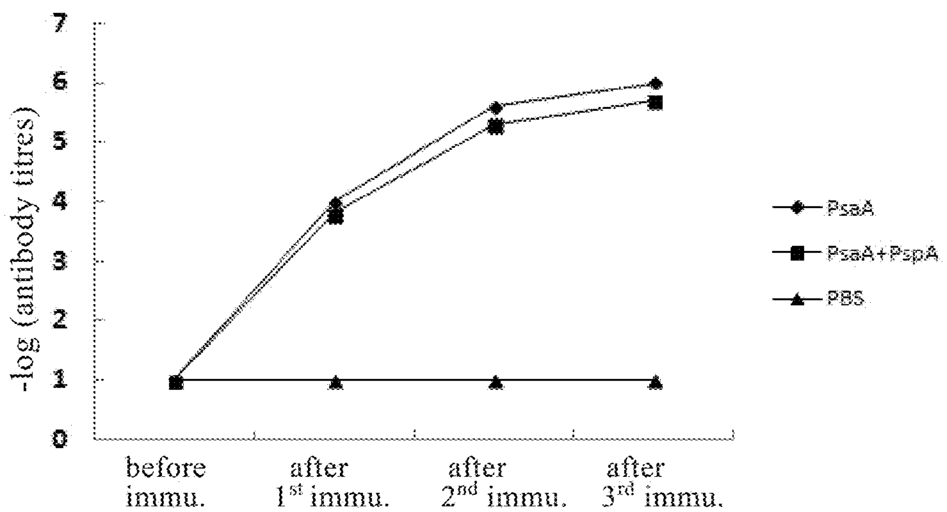
Figure 3.4

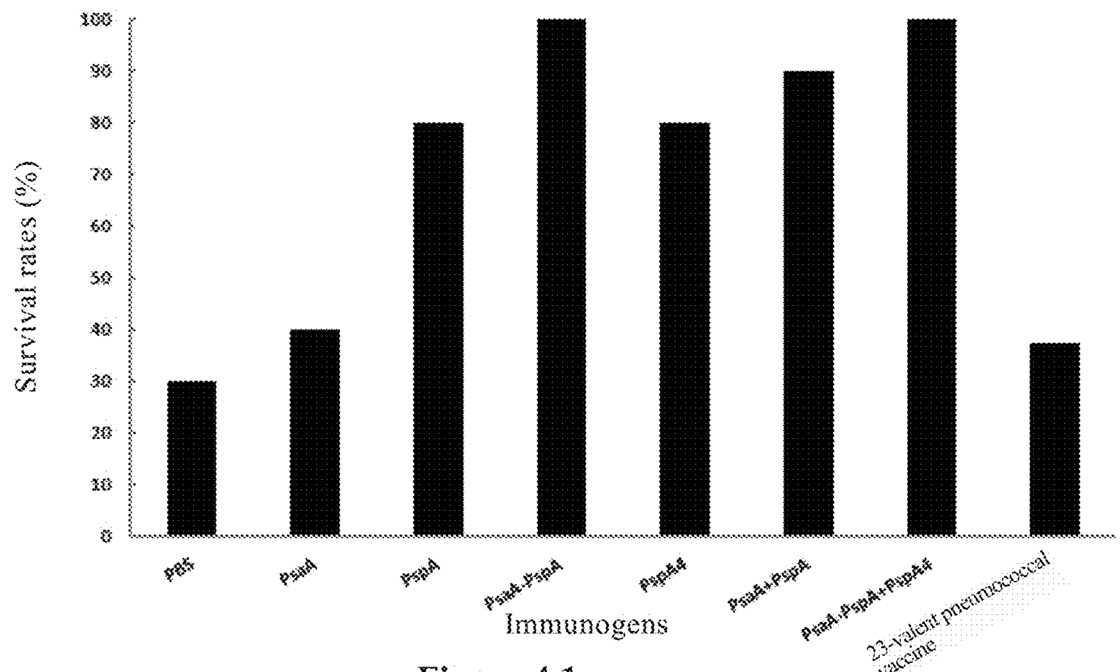
Figure 4.1
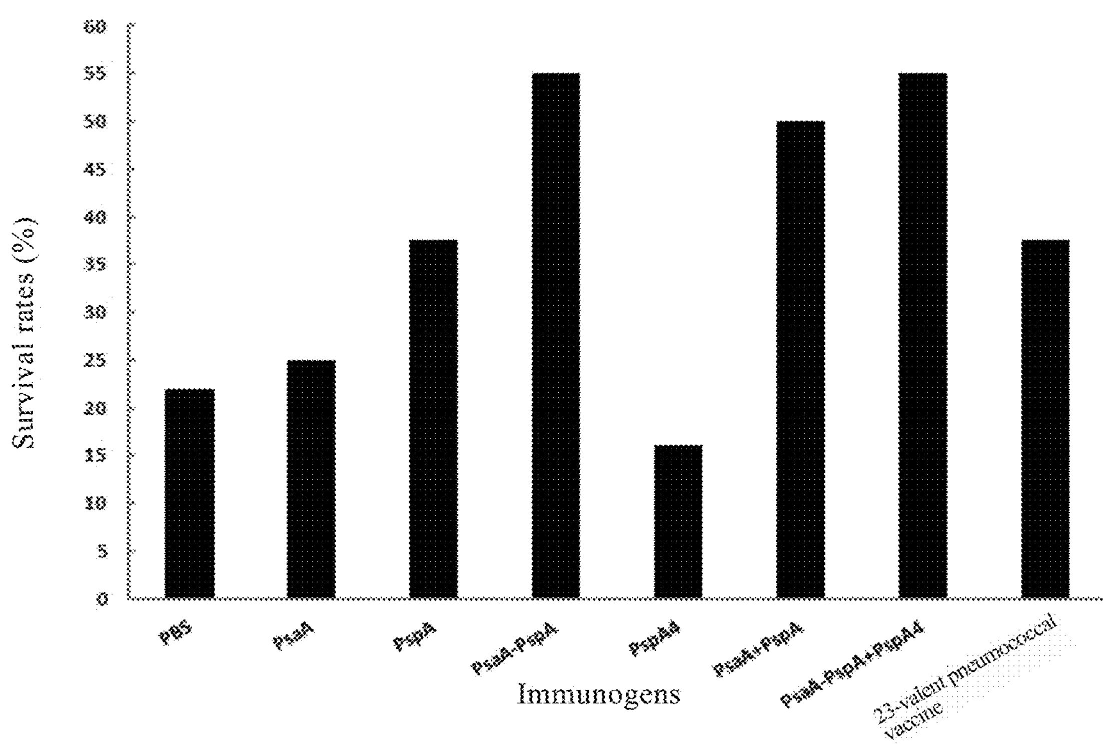
Figure 4.2

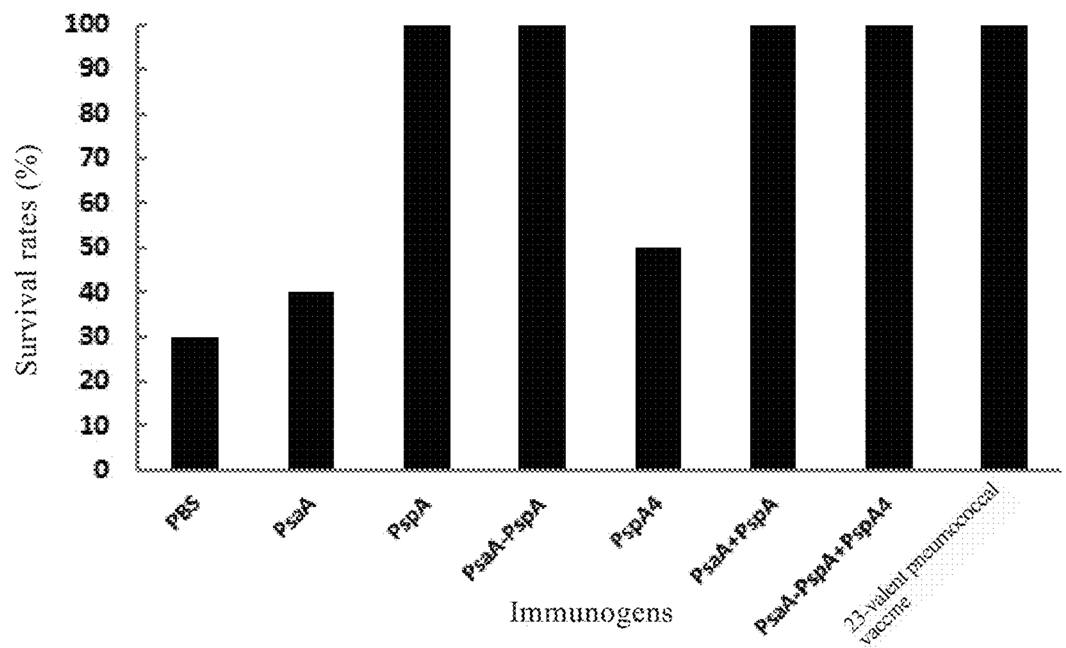
Figure 4.3
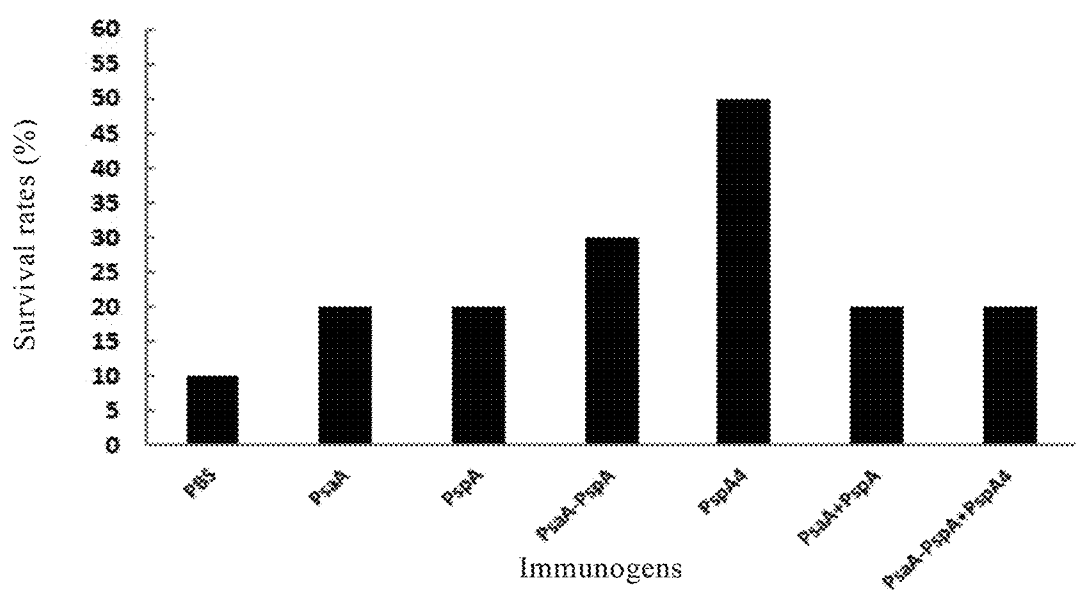
Figure 4.4

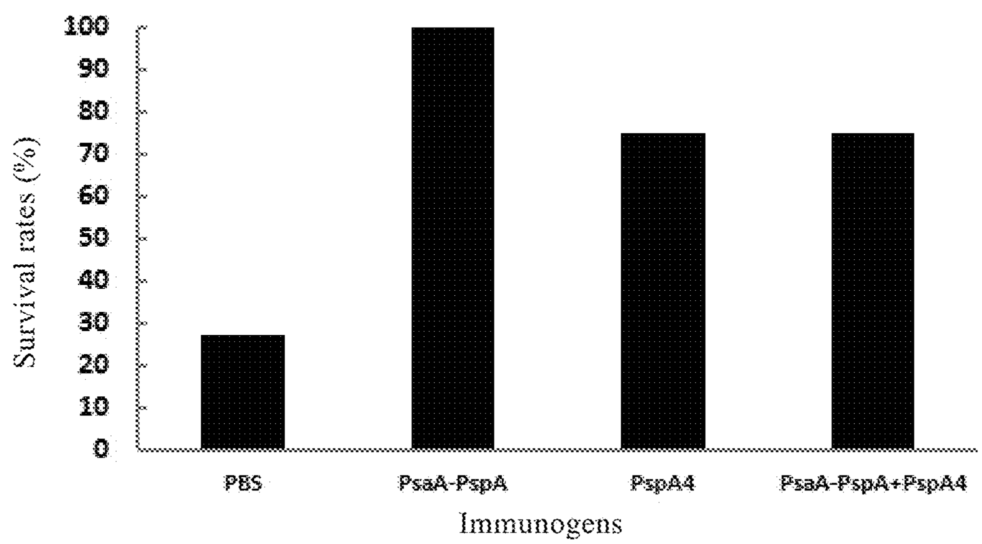
Figure 4.5
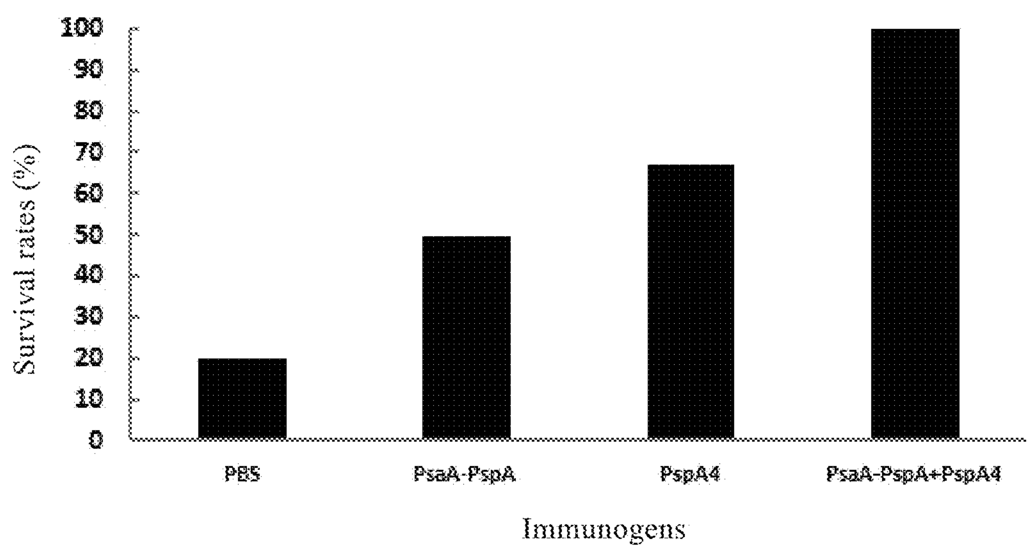
Figure 4.6

*STREPTOCOCCUS PNEUMONIAE* PROTEIN ANTIGEN, AND PREPARATION METHOD AND USE THEREOF

CROSS-REFERENCE TO RELATED APPLICATIONS

This application is a U.S. National Stage Application filed under 35 U.S.C. § 371 of International Application No. PCT/CN2016/077667, filed Mar. 29, 2016, which claims the benefit of Chinese Application No. 201510157541.X, filed Apr. 3, 2015. Both of these applications are hereby incorporated by reference in their entireties.

FIELD OF THE INVENTION

The present invention relates to the fields of molecular biology and immunology. In particular, the present invention relates to *Streptococcus pneumoniae* protein antigen, preparation method, composition and use thereof.

BACKGROUND OF THE INVENTION

1. *Streptococcus pneumoniae*

*Streptococcus pneumoniae* is a Gram-positive bacterium with capsular polysaccharide. As an ordinary pathogenic bacterium, it is the leading pathogenic agent of community-acquired pneumonia, and can also result in other diseases such as sinusitis, otitis media and meningitis. In developing countries, pneumonia caused by *Streptococcus pneumoniae* is one of the major causes of death in elderly people and young children: and in developed countries, otitis media caused by *Streptococcus pneumoniae* is also one of the most common diseases in the pediatric population. It was estimated that approximately one million children under age 5 worldwide died from diseases caused by *Streptococcus pneumoniae* in the year 2000. Christa L Fischer Walker et al. estimated that about fourteen million children under age 5 worldwide developed into severe pneumonia in the year 2010. *Streptococcus pneumoniae* is a leading pathogen of severe pneumonia; and throughout the world, at least 18% of severe cases and 33% of death cases caused by pneumonia are resulted from *Streptococcus pneumonia*.

2. Research Status of Current Pneumococcal Vaccines

At present, commercially available pneumococcal vaccines mainly include polysaccharide vaccines and polysaccharide-conjugate vaccines, both of which are pneumococcal capsular polysaccharide type-specific vaccines. Based on the difference of pneumococcal capsular polysaccharides, more than 90 different serotypes have been identified. Thus, pneumococcal vaccines based on polysaccharide cannot cover all the pneumococcal serotypes. The 23-valent pneumococcal capsular polysaccharide vaccine is ineffective to children under age 2 whose immune system has not been fully developed, and the 7-valent pneumococcal conjugate vaccine that has been widely used can only encompass 7 serotypes which account for 55% of pathogenic serotypes in Asia. Moreover, with the applications of polysaccharide vaccines and polysaccharide-conjugate vaccines, a phenomenon of serotype replacement has emerged, resulting in decreasing efficacy of vaccines year by year. Also, polysaccharide-conjugate vaccines are hardly available in developing countries owing to their high costs. Although the World Health Organization (WHO) recommended in 2007 that pneumococcal conjugate vaccines should be included in National Immunization Program in developing countries, this has not been materialized to date.

Pneumococcal protein vaccines have become the hot topic of current researches on pneumococcal vaccines because of their characteristics such as serotype independency, relatively lower costs, and good immunogenicity.

3. Pneumococcal Surface Adhesion A

Pneumococcal surface adhesion A (hereinafter referred to as "PsaA") is a highly-conserved, species-specific, surface-bound lipoprotein expressed by all strains of *Streptococcus pneumoniae*, and having a molecular weight of 37 KD and good immunogenicity. PsaA, which plays a vital role during manganese delivery and adherence of *Streptococcus pneumoniae* to mucosal membrane of respiratory tract, is an important virulence factor of *Streptococcus pneumoniae* invasion. It was reported that PsaA mutant affects many essential functions of *Streptococcus pneumoniae* including adhesion and virulence. PsaA exhibits excellent immunogenicity. Literatures reported that high-titre PsaA antibody can be induced either after PsaA immunization or after colonization of *Streptococcus pneumoniae* in nasopharynx, and also evaluated immune protective efficacy of PsaA. Therefore, PsaA protein, characterized by its species-specificity, sequence-conservatism, higher immunogenicity and immune protection, has become one of the hot topics in researches on *Streptococcus pneumoniae* protein vaccines.

4. Pneumococcal Surface Protein A

Pneumococcal surface protein A (hereinafter referred to as "PspA") is a bacterial surface protein belonging to the choline-binding protein family, and an important virulence factor of *Streptococcus pneumoniae*. PspA serves main functions of binding to lactoferrin to result in loss of its bacteriostatic activity and inhibiting complement deposition on the surface of *Streptococcus pneumoniae* so as to interfere in complement-mediated opsonization and phagocytosis. Studies have revealed that $PspA^-$ strain has lower virulence and is immediately cleared by body after infection. Actively-immunizing recombinant PspA protein can induce protection against various *Streptococcus pneumoniae* challenge models.

Currently, PspA was found to be present in all clinically isolated strains of *Streptococcus pneumoniae*. Nevertheless, such PspAs are not conservative in their molecular structures and have molecular weights varied from 67 to 100 KD. PspA molecule includes five regions: a signal peptide region, an α-helical region, a proline-rich region, a choline-binding region in which PspA binds to a cell surface, and a C-terminal tail of 17 amino acids.

Despite the variability of PspA in its structure and antigenicity, antibodies generated against PspA are highly cross-reactive and cross-protective. As shown by researches on gene and protein mapping, the majority of cross protection-conferring antigen epitopes are located in a sequence of approximately 100 amino acids adjacent to the proline-rich region in the α-helix region, which is called as a Clade Defining Region (hereinafter referred to as "CDR"). Based on the variations within the CDR regions, PspA is classified into three families (Fam1, Fam2 and Fam3), which are subdivided into 6 clades (Clade1, Clade2, Clade3, Clade4, Clade5 and Clade6), wherein Clade1 and Clade2 belong to Fam1; Clade3, Clade4 and Clade5 belong to Fam2, and Clade6 belongs to Fam3. Gene sequences of CDR regions in the clades of the same family share more than 80% identity; and gene sequences of CDR regions in different families share more than 50% identity. In the three families, Fam1 and Fam2 have prevalence of greater than 98%.

Most protein vaccines in the prior art utilize a single protein and can only act against certain category of *Streptococcus pneumoniae*, and thus do not have a broad spectrum. The present invention increases broad spectrum and protection of vaccines by using a fusion protein of PsaA and PspA, and using said fusion protein in combination with further protein antigens or as a protein carrier.

SUMMARY OF THE INVENTION

The inventors found that immunizing animals with a PsaA-PspA fusion protein can induce a high-titre antibody and confer good protection against challenge of strains from Fam1 and Fam2, as compared with control group (PBS): and the combined use of PsaA-PspA and Clade4 of PspA Fam2 (PspA4) can also afford good protection against challenge of strains from Fam1 and Fam2, as compared with control group (PBS).

In the first aspect, the present invention provides a fusion protein comprising pneumococcal surface adhesion A (PsaA) and pneumococcal surface protein A (PspA), wherein said PsaA is a full-length or truncated sequence of PsaA protein; and said PspA is a full-length or truncated sequence of any of Clade1, Clade2. Clade3, Clade4 and Clade5, or a fusion protein of all or part of the sequences of two or more PspA clades from Clade1, Clade2, Clade3, Clade4 and Clade5. Preferably, said PsaA and said PspA are ligated via a linker. Preferably, said different parts of PspA sequences are ligated via a linker. Preferably, said PsaA has an amino acid sequence as shown in SEQ ID NO: 1. Preferably, said PspA is a sequence obtained by ligating the amino acid sequence of the α-helical region of PspA Clade2 to that of the CDR region of PspA Clade3, and more preferably a sequence obtained by ligation via a linker; even more preferably, said PspA Clade2 has an N-terminal sequence as shown in SEQ ID NO: 2 and said PspA Clade3 has a hypervariable region with a sequence as shown in SEQ ID NO: 3. Most preferably, said PspA has a sequence as shown in SEQ ID NO: 4. Most preferably, said fusion protein has a sequence as shown in SEQ ID NO: 5.

In the second aspect, the present invention provides a nucleic acid encoding said fusion protein as described in the first aspect. Preferably, said nucleic acid is designed according to codon optimization, more preferably according to codon optimization favored by a prokaryotic cell, even more preferably according to codon optimization favored by *Escherichia coli* (*E. coli*), and most preferably has a sequence as shown in SEQ ID NO: 6.

In the third aspect, the present invention provides a recombinant expression vector comprising said nucleic acid as described in the second aspect that is operably linked to an expression regulatory element. Preferably, said expression vector is a plasmid, and more preferably a PET20b plasmid.

In the fourth aspect, the present invention provides a recombinant cell comprising said recombinant expression vector as described in the third aspect. Preferably, said cell is a prokaryotic cell, more preferably *E. coli*, and most preferably *E. coli* BL21.

In the fifth aspect, the present invention provides a method for preparing said PsaA-PspA fusion protein as described in the first aspect, comprising: inserting a nucleic acid encoding said PsaA-PspA into an expression vector; and introducing the resulting recombinant expression vector into an organism such that the nucleic acid is expressed to generate said fusion protein. Preferably, said method further comprises isolation and purification steps. More preferably, said fusion protein is purified by affinity chromatography, ion exchange chromatography and/or gel filtration chromatography.

In the sixth aspect, the present invention provides a composition comprising said fusion protein as described in the first aspect, said nucleic acid as described in the second aspect, the vector as described in the third aspect, or the cell as described in the fourth aspect, and a pharmaceutically acceptable carrier.

In the seventh aspect, the present invention provides a vaccine composition comprising said fusion protein as described in the first aspect, and preferably further comprising an adjuvant, and most preferably said adjuvant is an $Al(OH)_3$ adjuvant.

In the eighth aspect, the present invention provides a vaccine composition comprising said fusion protein as described in the first aspect and at least one further *Streptococcus pneumoniae* protein antigen. Preferably, said other protein antigen is a full-length or truncated sequence of a surface exposed protein, more preferably a full-length or truncated sequence of PspA, even more preferably a full-length or truncated sequence of PspA Clade4, and most preferably a sequence as shown in SEQ ID NO: 8. Preferably, said vaccine composition further comprises an adjuvant and more preferably an $Al(OH)_3$ adjuvant.

In the ninth aspect, the present invention provides use of said fusion protein alone or in combination with additional protein antigens in the manufacture of a vaccine for preventing infection by *Streptococcus pneumoniae.*

BRIEF DESCRIPTION OF THE FIGURES

FIG. 1.1 shows an electropherogram of the expression vector PET20b-PspA4 plasmid double-digested by Nde I and Xho I. 1: 1 kb DNA Ladder. 2: bands of PET20b-PspA4 plasmid after double enzymatic digestion with Nde I and Xho I. As shown in the figure, PET20b-PspA4 is confirmed by double enzymatic digestion to be in correct size, wherein the band at about 3700 bp is a linear fragment of an empty PET20b vector and the band at about 1300 bp is a PspA4 fragment of interest.

FIG. 1.2 shows an electropherogram of an expression vector PET20b-PsaA-PspA plasmid double-digested by Nde I and Xho 1. 1: 1 kb DNA Ladder. 2: bands of plasmid PET20b-PsaA-PspA after double enzymatic digestion with Nde I and Xho I. As shown in the figure, PET20b-PsaA-PspA is confirmed by double enzymatic digestion to be in correct size, wherein the band at about 3700 bp has a linear fragment of an empty PET20b vector and the band at about 2100 bp is a PsaA-PspA fragment of interest at about 2100 bp.

FIG. 1.3 shows an electropherogram of an expression vector PET20b-PspA plasmid double-digested by Nde I and Xho I. 1: 1 kb DNA Ladder. 2: bands of plasmid PET20b-PspA after double enzymatic digestion with Nde I and Xho I. As shown in the figure. PET20b-PspA is confirmed by double enzymatic digestion to be in correct size, wherein the band at about 3700 bp has a linear fragment of an empty PET20b vector and the band at about 1150 bp is a PspA fragment of interest.

FIG. 1.4 shows an electropherogram of an expression vector PET20b-PsaA plasmid double-digested by Nde I and Xho I. 1: 1 kb DNA Ladder. 2: bands of plasmid PET20b-PsaA after double enzymatic digestion with Nde I and Xho I. As shown in the figure, PET20b-PsaA is confirmed by double enzymatic digestion to be in correct size; the band at about 3700 bp has a linear fragment of an empty PET20b vector and the band at about 900 bp is a PsaA fragment of interest.

FIG. 2.1 shows a Sodium Dodecyl Sulfate-Polyacrylamide Gel Electrophoresis (SDS-PAGE) graph of purified PsaA-PspA fusion protein. 1: marker bands of eukaryotic protein. 2: band of PsaA-PspA fusion protein. As shown in the figure, the PsaA-PspA fusion protein has a size of 88.0 kD and a purity of about 82.0%.

FIG. 2.2 shows a SDS-PAGE graph of purified PspA4 protein. 1: marker bands of eukaryotic protein. 2: band of PspA4 protein. As shown in the figure, the PspA4 protein has a size of 63.8 kD and a purity of about 94.2%.

FIG. 2.3 shows a SDS-PAGE graph of purified PspA protein. 1: marker bands of eukaryotic protein; 2: band of PspA protein. As shown in the figure, the PspA protein has a size of 42.5 kD and a purity of about 88.0%.

FIG. 2.4 shows a SDS-PAGE graph of purified PsaA protein. 1: marker bands of eukaryotic protein. 2: band of PsaA protein. As shown in the figure, the PsaA protein has a size of 35.4 kD and a purity of about 86.0%.

FIG. 3.1 is a schematic graph showing the titres of the PsaA-PspA antibodies induced by immunizing mice with different antigens. Rhombus represents the titre of the PsaA-PspA antibody induced by subcutaneously immunizing mice with a mixture of a single PsaA-PspA fusion protein and an adjuvant $Al(OH)_3$. Square represents the titre of the PsaA-PspA antibody induced by subcutaneously immunizing mice with a mixture of a PsaA-PspA fusion protein, PspA4 and an adjuvant $Al(OH)_3$. Triangle represents the titre of the PsaA-PspA antibody induced by subcutaneously immunizing mice with a mixture of PBS as a control and an adjuvant $Al(OH)_3$. High-titre PsaA-PspA antibodies can be induced either by a single PsaA-PspA fusion protein or by a PsaA-PspA fusion protein in combination with PspA4, as compared with the control group.

FIG. 3.2 is a schematic graph showing the titres of the PspA4 antibodies induced by immunizing mice with different antigens. Rhombus represents the titre of the PspA4 antibody induced by subcutaneously immunizing mice with a mixture of a single PspA4 with an adjuvant $Al(OH)_3$. Square represents the titre of the PspA4 antibody induced by subcutaneously immunizing mice with a mixture of a PsaA-PspA fusion protein, PspA4 and an adjuvant $Al(OH)_3$. Triangle represents the titre of the PspA4 antibody induced by subcutaneously immunizing mice with a mixture of PBS as a control and an adjuvant $Al(OH)_3$. High-titre PspA4 antibodies can be induced either by a single PspA4 or PsaA-PspA in combination with PspA4, as compared with the control group.

FIG. 3.3 is a schematic graph showing the titres of the PspA antibodies induced by immunizing mice with different antigens. Rhombus represents the titre of the PspA antibody induced by subcutaneously immunizing mice with a mixture of a single PspA with an adjuvant $Al(OH)_3$. Square represents the titre of the PspA antibody induced by subcutaneously immunizing mice with a mixture of PsaA, PspA and an adjuvant $Al(OH)_3$. Triangle represents the titre of the PspA antibody induced by subcutaneously immunizing mice with a mixture of PBS as a control and an adjuvant $Al(OH)_3$. High-titre PspA antibodies can be induced either by a single PspA or by PsaA in combination with PspA, as compared with the control group.

FIG. 3.4 is a schematic graph showing the titres of the PsaA antibodies induced by immunizing mice with different antigens. Rhombus represents the titre of the PsaA antibody induced by subcutaneously immunizing mice with a mixture of a single PsaA and an adjuvant $Al(OH)_3$. Square represents the titre of the PsaA antibody induced by subcutaneously immunizing mice with a mixture of PsaA, PspA and an adjuvant $Al(OH)_3$. Triangle represents the titre of the PsaA antibody induced by subcutaneously immunizing mice with a mixture of PBS as a control and an adjuvant $Al(OH)_3$. High-titre PsaA antibodies can be induced either by a single PsaA or by PsaA in combination with PspA, as compared with the control group.

FIG. 4.1 is a bar graph showing survival rates of mice immunized with different antigens 14 days after challenged intraperitoneally with *Streptococcus pneumoniae* ATCC6404 strain (from Clade1 of PspA FAM1). Rectangular bars in the figure from left to right denote survival rates of mice immunized with PBS (control group), PsaA. PspA, a PsaA-PspA fusion protein, PspA4, PsaA in combination with PspA, a PsaA-PspA fusion protein in combination with PspA4, and a 23-valent pneumococcal polysaccharide vaccine, respectively.

FIG. 4.2 is a bar graph showing survival rates of mice immunized with different antigens 14 days after challenged intra-nasally with *Streptococcus pneumoniae* ATCC6404 strain (from Clade1 of PspA FAM1). Rectangular bars in the figure from left to right denote survival rates of mice immunized with PBS (control group), PsaA, PspA, a PsaA-PspA fusion protein, PspA4, PsaA in combination with PspA, a PsaA-PspA fusion protein in combination with PspA4, and a 23-valent pneumococcal polysaccharide vaccine, respectively.

FIG. 4.3 is a bar graph showing survival rates of mice immunized with different antigens 14 days after challenged intraperitoneally with *Streptococcus pneumoniae* ATCC10813 strain (from Clade2 of PspA Fam1). Rectangular bars in the figure from left to right denote survival rates of mice immunized with PBS (control group), PsaA, PspA, a PsaA-PspA fusion protein, PspA4, PsaA in combination with PspA, a PsaA-PspA fusion protein in combination with PspA4, and a 23-valent pneumococcal polysaccharide vaccine, respectively.

FIG. 4.4 is a bar graph showing survival rates of mice immunized with different antigens 14 days after challenged intraperitoneally with *Streptococcus pneumoniae* ATCC6314 strain (from Clade4 of PspA Fam2). Rectangular bars in the figure from left to right denote survival rates of mice immunized with PBS (control group), PsaA, PspA, a PsaA-PspA fusion protein, PspA4, PsaA in combination with PspA, and a PsaA-PspA fusion protein in combination with PspA4, respectively.

FIG. 4.5 is a bar graph showing survival rates of mice immunized with different antigens 14 days after challenged intraperitoneally with *Streptococcus pneumoniae* ATCC6303 strain (from Clade5 of PspA Fam2). Rectangular bars in the figure from left to right denote survival rates of mice immunized with PBS (control group), a PsaA-PspA fusion protein. PspA4, PsaA in combination with PspA, and a PsaA-PspA fusion protein in combination with PspA4, respectively.

FIG. 4.6 is a bar graph showing survival rates of mice immunized with different antigens 14 days after challenged intra-nasally with *Streptococcus pneumoniae* ATCC6303 strain (from Clade5 of PspA Fam2). Rectangular bars in the figure from left to right denote survival rates of mice immunized with PBS (control group), a PsaA-PspA fusion protein, PspA4, and a PsaA-PspA fusion protein in combination with PspA4, respectively.

DETAILED DESCRIPTION OF THE INVENTION

Advantages and technical effects of the present invention are illustrated in view of specific Examples in the text below.

The protection scope of the present invention is defined by the claims. The Examples are only intended to illustratively show the concept and principle of the present invention. It is to be understood that such specific embodiments will not be construed as limiting the scope of the present invention.

The present invention is illustrated in detail by means of the following Examples so that it can be more readily understood by those skilled in the art. Unless otherwise specified, it is to be understood that all the instruments or equipments used in the following Examples are those conventionally known in the art: the culture media used are commercially available conventional media of which the components and contents are well-known to those skilled in the art.

EXAMPLES

Example 1: Codon Optimization and Synthesis of the Nucleic Acid Sequence Encoding the Protein of Interest 1. Selection of the Amino Acid Sequence of PsaA-PspA Fusion Protein, Codon Optimization, and Synthesis of the Coding Nucleotide Sequence The sequences selected were as follows: an amino acid sequence of amino acids 20-309 of PsaA from *Streptococcus pneumoniae* strain D39 (GenBank: P0A4G2.1), as shown in SEQ ID NO: 1: an amino acid sequence of amino acids 32-319 of PspA (Clade2 of Fam1) from *Streptococcus pneumoniae* strain RX1 (GenBank: M74122.1), as shown in SEQ ID NO: 2: and an amino acid sequence of amino acids 346-420 of PspA (Clade3 of Fam2) from *Streptococcus pneumoniae* EF3296 (GenBank: AF071816.1), as shown in SEQ ID NO: 3. The PsaA-PspA fusion protein comprises a PspA protein portion obtained by ligating said amino acid sequence of amino acids 32-319 of PspA (Clade2 of Fam1) from *Streptococcus pneumoniae* strain RX1 and said amino acid sequence of amino acids 346-420 of PspA (Clade3 of Fam2) from *Streptococcus pneumoniae* EF3296 via a linker and having an amino acid sequence as shown in SEQ ID NO: 4. Said PsaA-PspA fusion protein has an amino acid sequence as shown in SEQ ID NO: 5 obtained by fusing SEQ ID NO: 1 and SEQ ID NO: 4 via a linker.

A nucleotide sequence encoding an amino acid sequence of the PsaA-PspA fusion protein was optimized by using the codon favored by *E. coli*, obtaining a nucleotide sequence as shown in SEQ ID NO: 6 encoding the PsaA-PspA fusion protein as shown in SEQ ID NO: 5. In order to facilitate enzymatic digestion, during synthesis of the nucleic acid, an Nde I digestion site and a six-histidine tag were introduced successively at 5' end; an Xho I digestion site was introduced at 3' end; and the resultant nucleotide sequence was shown in SEQ ID NO: 7.

A nucleotide sequence as shown in SEQ ID NO: 7 was artificially synthesized, and the synthesized sequence was stored in a pGH plasmid.

2. Selection of the Amino Acid Sequence of PspA4 Protein, Codon Optimization, and Synthesis of the Coding Nucleotide Sequence An amino acid sequence of amino acids 32-450 of PspA (Clade4 of Fam2) from *Streptococcus pneumoniae* EF5668 (GenBank: U89711.1) was selected, as shown in SEQ ID NO: 8.

A nucleotide sequence encoding an amino acid sequence of PspA4 protein was optimized with by using the codon favored by *E. coli*, obtaining a nucleotide sequence encoding PspA4 protein as shown in SEQ ID NO: 9. In order to facilitate enzymatic digestion, during synthesis of the nucleic acid, an Nde I digestion site was introduced at 5' end; an Xho I digestion site was introduced at 3' end; and the resultant nucleotide sequence was shown in SEQ ID NO: 10.

A nucleotide sequence as shown in SEQ ID NO: 10 was artificially synthesized, and the synthesized sequence was stored in a pGH plasmid.

3. Selection of the Amino Acid Sequence of PsaA Protein and Acquisition of the Coding Nucleotide Sequence An amino acid sequence of amino acids 20-309 of PsaA from *Streptococcus pneumoniae* strain D39 (GenBank: P0A4G2.1) was selected, as shown in SEQ ID NO: 1. In order to facilitate enzymatic digestion, in the nucleotide sequence encoding the amino acid sequence as shown in SEQ ID NO: 1, an Nde I digestion site was introduced at 5' end by means of PCR technique; and an Xho I digestion site was introduced at 3' end.

A nucleotide sequence as shown in SEQ ID NO: 11 was obtained by means of PCR technique using the artificially-synthesized nucleotide sequence of PsaA-PspA fusion protein as shown in SEQ ID NO: 7 as template, the sequence as shown in SEQ ID NO: 13 as 5'-primer, and the sequence as shown in SEQ ID NO: 14 as 3'-primer.

The system for PCR reaction comprises:

| | |
|---|---|
| 5'-primer | 1 μL |
| 3'-primer | 1 μL |
| Template | 1 μL |
| Taq enzyme | 0.5 μL |
| 10× PCR reaction buffer | 5 μL |
| dNTP (10 mmol) | 1 μL |
| $MgSO_4$ (50 mmol) | 1.5 μL |
| water | 39 μL |

The conditions for PCR reaction are as follows:

| | |
|---|---|
| 94° C. | 5 min |
| 94° C. 30 s, 58° C. 30 s, 72° C. 60 s, totaling 30 cycles | |
| 72° C. | 10 min |

The PsaA nucleotide sequence amplified by PCR that had been confirmed to have the correct sequence was ligated into T-easy carrier (available from PROMEGA).

Ligation system:

| | |
|---|---|
| T-easy | 1 μL |
| PCR product | 0.5 μL |
| T4 ligase | 0.5 μL |
| 10× T4 buffer | 5 μL |
| water | 3 μL |

Condition: 16° C. overnight.

Ligation products were transformed into *E. coli* Top 10 (available from Tiangen BioTech Co. Ltd.) on the next day, then plated and incubated at 37° C. overnight. A single colony was picked and incubated in 5 ml LB medium overnight. Subsequently, plasmids were extracted using Plasmid Extraction Kit and sequenced. The plasmid confirmed to have the correct sequence was used for enzymatic digestion.

4. Selection of the Amino Acid Sequence of PspA Protein and Acquisition of the Coding Nucleotide Sequence The sequences selected were as follows: an amino acid sequence of amino acids 32-319 of PspA (Clade2 of Fam1) from *Streptococcus pneumoniae* strain RX1 (GenBank: M74122.1), as shown in SEQ ID NO: 2; and an amino acid sequence of amino acids 346-420 of PspA (Clade3 of Fam2) from *Streptococcus pneumoniae* EF3296 (GenBank: AF071816.1), as shown in SEQ ID NO: 3. PspA protein was obtained by ligating the above two amino acid sequences via a linker and has an amino acid sequence as shown in SEQ ID NO: 4. In order to facilitate enzymatic digestion, in the nucleotide sequence encoding the amino acid sequence as shown in SEQ ID NO: 4, an Nde I digestion site was introduced at 5' end; and an ho I digestion site was introduced at 3' end.

A nucleotide sequence as shown in SEQ ID NO: 12 was obtained by means of PCR technique using the artificially-synthesized nucleotide sequence of PsaA-PspA fusion protein as shown in SEQ ID NO: 7 as template, the sequence as shown in SEQ ID NO: 15 as 5'-primer, and the sequence as shown in SEQ ID NO: 16 as 3'-primer.

The system for PCR reaction comprise:

| | |
|---|---|
| 5'-primer | 1 μL |
| 3'-primer | 1 μL |
| Template | 1 μL |
| Taq enzyme | 0.5 μL |
| 10× PCR buffer | 5 μL |
| dNTP (10 mmol) | 1 μL |
| $MgSO_4$ (50 mmol) | 1.5 μL |
| water | 39 μL |

The conditions for PCR reaction are as follows:

| | |
|---|---|
| 94° C. | 5 min |
| 94° C. 30 s, 57° C. 30 s, 72° C. 90 s, totaling 30 cycles | |
| 72° C. | 10 min |

The PspA nucleotide sequence amplified by PCR that had been confirmed to have the correct sequence was ligated into T-easy carrier (available from PROMEGA).

Ligation system:

| | |
|---|---|
| T-easy | 1 μL |
| PCR product | 0.5 μL |
| T4 ligase | 0.5 μL |
| 10× T4 buffer | 5 μL |
| water | 3 μL |

Condition: 16° C. overnight.

Ligation products were transformed into *E. coli* Top 10 (available from Tiangen BioTech Co. Ltd.) on the next day, then plated and incubated at 37° C. overnight. A single colony was picked and incubated in 5 ml LB medium overnight. Subsequently, plasmids were extracted using Plasmid Extraction Kit and sequenced. The plasmid confirmed to have the correct sequence was used for enzymatic digestion.

Example 2: Expression and Purification of Protein

1. Construction of Expression Vector

Plasmid bearing a nucleic acid encoding PsaA-PspA with correct sequence (SEQ ID NO: 7) was double-digested with Nde I and Xho I and ligated via T4 ligase (available from PROMEGA) into an expression vector PET20b (available from Novagen Ltd.) treated by the same double-digestion. Litigation products were then transformed into *E. coli* Top 10 (available from Tiangen BioTech Co. Ltd.) and plated onto a plate of LB medium (containing 50 μg/ml ampicillin) for incubation overnight. Colonies were picked on the next day and added into LB medium (containing 50 μg/ml ampicillin) for incubation overnight. Plasmids were extracted on the following day. After double-digestion with Nde I and Xho I, colonies confirmed to be correct by enzymatic digestion were sequenced to pick the colonies having the sequences of interest, thereby obtaining the expression plasmid PET20b-PsaA-PspA. Similarly, PET20b-PspA4 plasmid was obtained from the plasmids comprising a nucleic acid encoding PspA4 protein with correct sequence (SEQ ID NO: 10).

T-easy vector bearing a nucleic acid encoding PsaA protein with correct sequence (SEQ ID NO: 11) was double-digested with Nde I and Xho I and ligated via T4 ligase (available from PROMEGA) into an expression vector PET20b (available from Novagen Ltd.) treated by the same double-digestion. Litigation products were then transformed into *E. coli* Top 10 (available from Tiangen BioTech Co. Ltd.) and plated onto a plate of LB medium (containing 50 μg/ml ampicillin) for incubation overnight. Colonies were picked on the next day and added into LB medium (containing 50 μg/ml ampicillin) for incubation overnight. Plasmids were extracted on the following day. After double-digestion with Nde I and Xho I, colonies confirmed to be correct by enzymatic digestion were sequenced to pick the colonies having the sequences of interest, thereby obtaining the expression plasmid PET20b-PsaA. Similarly, Expression plasmid PET20b-PspA was obtained from the T-easy vectors comprising a nucleic acid encoding PspA protein with correct sequence (SEQ ID NO: 12).

Expression plasmids PET20b-PspA4, PET20b-PsaA-PspA, PET20b-PspA and PET20b-PsaA were confirmed by enzymatic digestion with Nde I and Xho I to have fragments in correct size. Enzymatic digestion results are shown in FIGS. 1.1 to 1.4, respectively. Plasmids confirmed to be correct by enzymatic digestion were sequenced to select the expression plasmids with correct sequence.

2. Expression of the Proteins of Interest, PsaA-PspA Fusion Protein, PspA4 Protein, PsaA Protein and PspA Protein, in Host Bacteria Recombinant expression plasmids with correct sequences, PET20b-PspA4, PET20b-PsaA-PspA, PET20b-PspA and PET20b-PsaA, were transformed into *E. coli* BL21 (DE3) competent cells (available from TransGen Biotech). LB agar plate (containing 50 μg/ml ampicillin) was used for screening the cells. Fresh single colonies were picked and inoculated into 5 ml LB medium (containing 50 μg/ml ampicillin) for incubation overnight with shaking at 37° C. 50 μl of overnight cultures were taken out on the next day and then were incubated in 5 ml of fresh LB medium (containing 50 μg/ml ampicillin) for incubation with shaking at 37° C. for about 3 hours. When $OD_{600}$ reaches about 0.4 to 0.6, isopropyl-thiogalactoside (IPTG) at a final concentration of 1 mM was added to induce expression at 37° C. for 5 to 6 hours (IPTG was not added in the control group). Bacteria were harvested by centrifugation at 12000 rpm/minute at 4° C. for 5 min. Expression of protein of interest was determined by SDS-PAGE and Western blotting.

3. Incubation and Amplification of Expression Host

Colonies with high levels of protein expression were amplified and incubated. The overnight cultures were inoculated into 500 ml fresh LB medium (containing 50 μg/ml ampicillin) in a ratio of 1:50 for incubation with shaking at 37° C. for about 3 hours. When $OD_{600}$ reaches about 0.4 to 0.6, isopropyl-thiogalactoside (IPTG) at a final concentration of 1 mM was added to induce expression at 37° C. for 5 to 6 hours (IPTG was not added in the control group). Bacterial culture medium with significant expression was selected and centrifuged at 6000 rpm/minute at 4° C. for 30 min, cell precipitates were harvested, and supernatants were discarded.

4. Isolation and Purification of Expression Product of Interest

Cell precipitates were re-suspended in bacterial lysis buffer (50 mM Tris(hydroxymethyl)aminomethane hydrochlorate (Tris-HCl) and 1 mM Ethylene Diamine Tetraacetic Acid (EDTA), pH 8.0), broken by sonication in ice bath for 15 min, and centrifuged at 10000 rpm/minute at 4° C. for 30 min. Supernatants were collected, filtered with microporous filtration membrane having a pore size of 0.45 μm, and purified by affinity chromatography in an Ni-NTA column (GE Healthcare). Initially, 50 mM Tris-HCl buffer (pH 8.0) was used to balance the Ni-NTA column. Next, the supernatants were dripped onto the column at a speed of 1.5 ml/min. Gradient elution was carried out using elution buffers (50 mM Tris-HCl buffers (pH 8.0) comprising 50, 100, 200, and 500 mM imidazole, successively). Eluents were collected for each gradient and analyzed by SDS-PAGE to obtain their purity. SDS-PAGE result of purified PsaA-PspA fusion protein was shown in FIG. 2.1 with the purity of 82.0%. SDS-PAGE result of purified PspA4 was shown in FIG. 2.2 with the purity of 94.2%. SDS-PAGE result of purified PspA protein was shown in FIG. 2.3 with the purity of 88.0%. SDS-PAGE result of purified PsaA protein was shown in FIG. 2.4 with the purity of 86.0%.

Said proteins of interest were also isolated and purified by ion exchange chromatography and gel filtration chromatography to obtain the proteins of interest with higher purity (results not shown).

Conclusion: through the experiments described in this Example, it can be seen that various proteins of interest with the purity of 80% or more could be obtained.

Example 3: Immunogenicity Assessment of PsaA-PspA Fusion Protein, PspA4 Protein, PspA Protein, and PsaA Protein After purification, the PsaA-PspA fusion protein alone, PspA4 protein alone, PspA protein alone, PsaA protein alone, PsaA-PspA fusion protein in combination with PspA4 protein, and PspA protein in combination with PsaA protein in PBS were respectively mixed with adjuvant $Al(OH)_3$ homogeneously. As a control, an equal volume of PBS was homogeneously mixed with adjuvant $Al(OH)_3$. Said PsaA-PspA fusion protein and PspA4 protein, either alone or in combination for immunization, are used in a dose of 20 μg/mouse, said PspA protein and PsaA protein, either alone or in combination for immunization, are used in a dose of 10 μg/mouse: adjuvant $Al(OH)_3$ is used in a dose of 100 μg/mouse; and the total volume is 100 μL/mouse. Seventy 6- to 8-week-old female BALB/c mice were randomized into seven groups (10 mice in each group). Said seven groups of mice were immunized subcutaneously at three sites in the back with the above seven groups of mixtures, totaling three immunizations with two-week intervals.

Sera were collected before immunization and 12 days after every immunization. Antibody levels in the serum were measured by enzyme-linked immunosorbent assay (ELISA). At first, ELISA plates were coated with purified antigens for ELISA assay as shown in Table 1 and incubated at 4° C. overnight. On the next day, the ELISA plates were blocked with 3% bovine serum albumin (BSA) and incubated for 2 hours. Subsequently, immune serum diluted in a 10-fold series was added and incubated at 37° C. for 45 min. After washing the ELISA plates with PBS-T (pH 7.4, 0.5% Tween20), 100 μL horseradish peroxidase (HRP)-labeled goat anti-mouse antibody in 1:10000 dilution (Beijing Ding Guo Chang Sheng Biotech Co. Ltd), as second antibody, was added and incubated at 37° C. for 45 min. After the plate washing, the plates were developed for 15 min by adding tetramethyl benzidine (TMB, available from Beijing Ding Guo Chang Sheng Biotech Co. Ltd). When the development was finished, 2 mol/L $H_2SO_4$ was added to stop the reaction. Absorbtance was monitored at a wavelength of 450 nm using a microplate reader (Bio-Rad Laboratories, Inc.). Antibody titre is the negative logarithm of serum antibody titre. The serum antibody titres for each group of the immunized mice were shown in FIGS. 3.1 to 3.4.

TABLE 1

Immunogens used in immunogenicity assay and antigens for ELISA assay

| ELISA group | Immunogen | Antigen for ELISA assay |
|---|---|---|
| 1 | PsaA-PspA | PsaA-PspA |
| 2 | PsaA-PspA + PspA4 | PsaA-PspA |
| 3 | PspA4 | PspA4 |
| 4 | PsaA-PspA + PspA4 | PspA4 |
| 5 | PspA | PspA |
| 6 | PsaA-PspA | PspA |
| 7 | PspA | PsaA |
| 8 | PsaA-PspA | PsaA |

Conclusion: as shown in FIGS. 3.1 to 3.4, high-titre serum antibodies can be induced by immunization with a PsaA-PspA fusion protein, a PspA4 protein alone, a combination of a PsaA-PspA fusion protein and a PspA4 protein, a PsaA protein, a PspA protein alone, or a combination of a PspA4 protein and a PsaA protein, as compared with the control group.

Example 4: Immune Protection of the Protein of Interest

1. Challenge with PspA Fam1

After purification, the PsaA-PspA fusion protein, PspA4 protein alone, PspA protein alone, PsaA protein alone, PsaA-PspA fusion protein in combination with PspA4 protein, and PspA protein in combination with PsaA protein were respectively mixed with adjuvant $Al(OH)_3$ homogeneously. As a negative control, an equal volume of PBS was homogeneously mixed with adjuvant $Al(OH)_3$. Said PsaA-PspA fusion protein and PspA4 protein, either alone or in combination for immunization, are used in a dose of 20 μg/mouse; said PspA protein and PsaA protein, either alone or in combination for immunization, are used in a dose of 10 μg/mouse; adjuvant $Al(OH)_3$ is used in a dose of 100 μg/mouse; and the total volume is 100 μL/mouse. Seventy 6- to 8-week-old female BALB/c mice were randomized into seven groups (10 mice in each group). Said seven groups of mice were immunized subcutaneously at three sites in the back with the above seven groups of mixtures, totaling three immunizations with two-week interval between two immunizations. As a positive control, the commercially available 23-valent pneumococcal polysaccharide vaccine was used. The mice were subcutaneously immunized in the back only once in a dose of one-fifth human dose, i.e., 100 μL per mouse (in accordance with instructions for administering vaccine) when performing the first immunization (hereinafter referred to as "1$^{st}$ immu.") of the protein groups. On day 14 after the last immunization, the mice were challenged intraperitoneally or intra-nasally with *Streptococcus pneu-*

*moniae* ATCC6404 strain (from Clade1 of PspA Fam1) or *Streptococcus pneumoniae* ATCC10813 strain (from Clade2 of PspA Fam1) (both strains are available from American Type Culture Collection) in a lethal dose. Mice were observed for survival over a period of 14 days following the challenge. Mice challenged intraperitoneally (in a dose of 100 (CFU/mouse) and inter-nasally (in a dose of $1.6\times10^9$ CFU/mouse) with *Streptococcus pneumoniae* ATCC6404 strain (from Clade1 of PspA Fam1) were observed for their survival rates after 14 days. Mice challenged intraperitoneally with *Streptococcus pneumoniae* ATCC10813 strain (from Clade2 of PspA Fam1) in a dose of 20 CFU/mouse were observed for their survival rates after 14 days. As shown in FIGS. 4.1 to 4.3, the results are as follows:

(1) Mice immunized with PsaA, PspA, PsaA-PspA fusion protein, PspA4, PsaA in combination with PspA. PsaA-PspA fusion protein in combination with PspA4, or 23-valent pneumococcal polysaccharide vaccine have higher survival rates than those in the control group (PBS).

(2) PsaA-PspA fusion protein confers higher protection against the challenge with *Streptococcus pneumoniae* ATCC6404 strain (from Clade1 of PspA Fam1) or *Streptococcus pneumoniae* ATCC10813 strain (from Clade2 of PspA Fam1) than PsaA or PspA alone.

(3) As compared with PsaA in combination with PspA, PsaA-PspA fusion protein confers similar protection against the challenge with *Streptococcus pneumoniae* ATCC10813 strain (from Clade2 of PspA Fam1) and higher protection against the challenge with *Streptococcus pneumoniae* ATCC6404 strain (from Clade1 of PspA Fam1).

(4) As compared with 23-valent pneumococcal polysaccharide vaccine, mice immunized with PsaA-PspA fusion protein or PsaA-PspA fusion protein in combination with PspA4 display higher survival rates and higher protection against the challenge with *Streptococcus pneumoniae* ATCC6404 strain (from Clade1 of PspA Fam1).

(5) PsaA-PspA fusion protein alone, either administered intra-nasally or intraperitoneally, confers good protection against the challenge with Clade1 of Fam1 and also good protection against the intraperitoneal challenge with Clade2 of Fam1. In particular, said fusion protein can achieve up to 100% protection against the intraperitoneal challenge with Clade1 and Clade2.

(6) As compared with PspA4, PsaA-PspA fusion protein confers higher protection against the challenge with Clade1 and Clade2 of PspA Fam1 and better cross-protection against the bacteria strain from Fam1.

Thus, PsaA-PspA fusion protein, either used alone or in combination with PspA4, can confer significant protection against the challenge with Clade1 and Clade2 of PspA Fam1.

2. Challenge with PspA Fam2

After purification, the PsaA-PspA fusion protein, PspA4 protein alone, PspA protein alone, PsaA protein alone, PsaA-PspA fusion protein in combination with PspA4 protein, and PspA protein in combination with PsaA protein were respectively mixed with adjuvant $Al(OH)_3$ homogeneously. As a negative control, an equal volume of PBS was homogeneously mixed with adjuvant $Al(OH)_3$. Said PsaA-PspA fusion protein and PspA4 protein, either alone or in combination for immunization, are used in a dose of 20 μg/mouse, said PspA protein and PsaA protein, either alone or in combination for immunization, are used in a dose of 10 μg/mouse; adjuvant $Al(OH)_3$ is used in a dose of 100 μg/mouse; and the total volume is 100 μL/mouse. 6- to 8-week-old female BALB/c mice (10 mice in each group) were subcutaneously immunized at three sites in the back, totaling three immunizations with two-week interval between two immunizations. On day 14 after the last immunization, the mice were challenged intraperitoneally or intranasally with *Streptococcus pneumoniae* ATCC6314 strain (from Clade4 of PspA Fam2) or *Streptococcus pneumoniae* ATCC6303 strain (from Clade5 of PspA Fam2) (both strains are available from American Type Culture Collection) in a lethal dose. Mice were observed for survival over a period of 14 days following the challenge.

Mice survival rates 14 days after the intraperitoneal challenge with *Streptococcus pneumoniae* ATCC6314 strain (from Clade4 of PspA Fam2) (in a dose of $6\times10^7$ CFU/mouse), and mice survival rates 14 days after intraperitoneal challenge (in a dose of 20 CFU/mouse) and inter-nasal challenge (in a dose of $2.2\times10^6$ CFU/mouse) with *Streptococcus pneumoniae* ATCC6303 strain (from Clade5 of PspA Fam2) were shown in FIGS. 4.4, 4.5 and 4.6, respectively. The results are as follows:

(1) Mice immunized with PsaA. PspA, PsaA-PspA fusion protein, PspA4, PsaA in combination with PspA, and PsaA-PspA fusion protein in combination with PspA4 have higher survival rates than those in the control group (PBS).

(2) PsaA-PspA fusion protein confers higher protection against the challenge with *Streptococcus pneumoniae* ATCC6314 strain (from Clade4 of PspA FAMam2) than PsaA or PspA alone.

(3) As compared with PsaA in combination with PspA, PsaA-PspA fusion protein confers higher protection against the challenge with *Streptococcus pneumoniae* ATCC6314 strain (from Clade4 of PspA Fam2).

(4) PsaA-PspA fusion protein alone confers good protection against the challenge with Clade4 and Clade5 of Fam2, no matter challenged intra-nasally or intraperitoneally.

(5) As compared with PspA4, PsaA-PspA fusion protein confers lower protection against the intraperitoneal challenge with Clade4 of PspA Fam2 or intra-nasal challenge with Clade5 of PspA Fam2. The reason why PspA4 protein affords better protection against virus strain of Fam2 is that the PspA in the fusion protein is the N-terminal sequence of the RX1 strain from Clade2 of PspA Fam1, while the PspA4 protein has the sequence of Clade4 of Fam2. Nevertheless, PsaA-PspA fusion protein confers better protection against the intraperitoneal challenge with Clade5 of PspA Fam2 than PspA4.

(6) As compared with PsaA-PspA fusion protein alone, PsaA-PspA fusion protein in combination with PspA4 confers significantly higher protection against the intra-nasal challenge with Clade5 of PspA Fam2.

CONCLUSION

The experiments in this Example indicated that PsaA-PspA fusion protein confers significantly higher protection against the challenge with virus strains from Fam1 and Fam2; and PspA4 protein alone gives lower protection against Fam1. Thus, the PsaA-PspA fusion protein of the present invention can be used either as an immunogen or as a vaccine in combination with an adjuvant.

PsaA-PspA fusion protein in combination with PspA4 has good protection against bacteria strains from Fam1 and Fam2. The PsaA-PspA fusion protein of the present invention can also be used in combination with other surface proteins. Thus, PsaA-PspA fusion protein is a good candidate immunogen for *Streptococcus pneumoniae* vaccine and is capable of achieving better protective efficacy when combined with other proteins.

The PsaA-PspA fusion protein of the present invention can also be used as a carrier protein in polysaccharide vaccines to increase broad spectrum and protection of such vaccines.

The invention claimed is:

1. A fusion protein comprising a Pneumococcal surface adhesion A (PsaA) and a Pneumococcal surface protein A (PspA), wherein the PsaA has an amino acid sequence as shown in SEQ ID NO: 1; and the PspA comprises a part of PspA Clade2 wherein said part of PspA Clade2 comprises SEQ ID NO: 2 and a part of PspA Clade3 wherein said part of PspA Clade3 comprises SEQ ID NO: 3.

2. The fusion protein of claim 1, wherein the PsaA and the PspA, the PspA Clade 2 and Clade 3, are ligated via a linker.

3. The fusion protein of claim 1, wherein the PspA has an amino acid sequence as shown in SEQ ID NO: 4.

4. The fusion protein of claim 1, wherein the fusion protein has an amino acid sequence as shown in SEQ ID NO: 5.

5. A nucleic acid encoding the fusion protein according to claim 1.

6. The nucleic acid of claim 5, wherein the nucleic acid is designed via codon optimization favored by *E. coli.*

7. The nucleic acid of claim 5, wherein the nucleic acid has a polynucleotide sequence as shown in SEQ ID NO:6.

8. A recombinant expression vector comprising the nucleic acid according to claim 5.

9. A cell comprising the expression vector according to claim 8.

10. A method for preparing the fusion protein according to claim 1, comprising: inserting a nucleic acid encoding the fusion protein into an expression vector, and introducing the resultant recombinant expression vector into a cell such that the nucleic acid is expressed to generate the fusion protein.

11. The method of claim 10, further comprising isolating and purifying the fusion protein, wherein the step of purifying the fusion protein comprises affinity chromatography, ion exchange chromatography, gel filtration chromatography, or combinations thereof.

12. A composition comprising a pharmaceutically acceptable carrier and one or more of: the fusion protein according to claim 1, a nucleic acid encoding the fusion protein, a recombinant expression vector comprising the nucleic acid; and a cell comprising the expression vector.

13. A vaccine composition comprising the fusion protein according to claim 1 and at least one other *Streptococcus pneumoniae* protein antigen.

14. The vaccine composition of claim 13, wherein the other *Streptococcus pneumoniae* protein antigen is a full-length amino acid sequence of a surface exposed protein.

15. The vaccine composition of claim 13, wherein the other *Streptococcus pneumoniae* protein antigen has an amino acid sequence as shown in SEQ ID NO:8.

16. An vaccine composition comprising the fusion protein according to claim 1 and an adjuvant.

17. The vaccine composition of claim 16, wherein the adjuvant is an aluminum adjuvant.

18. A method for preventing *Streptococcus pneumoniae* infection in a subject, comprising administrating the fusion protein according to claim 1 alone or in combination with other *Streptococcus pneumoniae* protein antigens to the subject.

* * * * *

SEQUENCE LISTING

```
<160> NUMBER OF SEQ ID NOS: 16

<210> SEQ ID NO 1
<211> LENGTH: 290
<212> TYPE: PRT
<213> ORGANISM: Streptococcus pneumoniae D39

<400> SEQUENCE: 1

Cys Ala Ser Gly Lys Lys Asp Thr Thr Ser Gly Gln Lys Leu Lys Val
1               5                   10                  15

Val Ala Thr Asn Ser Ile Ile Ala Asp Ile Thr Lys Asn Ile Ala Gly
            20                  25                  30

Asp Lys Ile Asp Leu His Ser Ile Val Pro Ile Gly Gln Asp Pro His
        35                  40                  45

Glu Tyr Glu Pro Leu Pro Glu Asp Val Lys Lys Thr Ser Glu Ala Asp
    50                  55                  60

Leu Ile Phe Tyr Asn Gly Ile Asn Leu Glu Thr Gly Gly Asn Ala Trp
65                  70                  75                  80

Phe Thr Lys Leu Val Glu Asn Ala Lys Lys Thr Glu Asn Lys Asp Tyr
                85                  90                  95

Phe Ala Val Ser Asp Gly Val Asp Val Ile Tyr Leu Glu Gly Gln Asn
            100                 105                 110

Glu Lys Gly Lys Glu Asp Pro His Ala Trp Leu Asn Leu Glu Asn Gly
        115                 120                 125

Ile Ile Phe Ala Lys Asn Ile Ala Lys Gln Leu Ser Ala Lys Asp Pro
    130                 135                 140

Asn Asn Lys Glu Phe Tyr Glu Lys Asn Leu Lys Glu Tyr Thr Asp Lys
145                 150                 155                 160

Leu Asp Lys Leu Asp Lys Glu Ser Lys Asp Lys Phe Asn Lys Ile Pro
                165                 170                 175

Ala Glu Lys Lys Leu Ile Val Thr Ser Glu Gly Ala Phe Lys Tyr Phe
            180                 185                 190

Ser Lys Ala Tyr Gly Val Pro Ser Ala Tyr Ile Trp Glu Ile Asn Thr
        195                 200                 205

Glu Glu Glu Gly Thr Pro Glu Gln Ile Lys Thr Leu Val Glu Lys Leu
    210                 215                 220

Arg Gln Thr Lys Val Pro Ser Leu Phe Val Glu Ser Ser Val Asp Asp
225                 230                 235                 240

Arg Pro Met Lys Thr Val Ser Gln Asp Thr Asn Ile Pro Ile Tyr Ala
                245                 250                 255

Gln Ile Phe Thr Asp Ser Ile Ala Glu Gln Gly Lys Glu Gly Asp Ser
            260                 265                 270

Tyr Tyr Ser Met Met Lys Tyr Asn Leu Asp Lys Ile Ala Glu Gly Leu
        275                 280                 285

Ala Lys
    290


<210> SEQ ID NO 2
<211> LENGTH: 288
<212> TYPE: PRT
<213> ORGANISM: Streptococcus pneumoniae RX1
```

<400> SEQUENCE: 2

```
Glu Glu Ser Pro Val Ala Ser Gln Ser Lys Ala Glu Lys Asp Tyr Asp
1               5                   10                  15

Ala Ala Lys Lys Asp Ala Lys Asn Ala Lys Lys Ala Val Glu Asp Ala
            20                  25                  30

Gln Lys Ala Leu Asp Asp Ala Lys Ala Ala Gln Lys Lys Tyr Asp Glu
        35                  40                  45

Asp Gln Lys Lys Thr Glu Glu Lys Ala Ala Leu Glu Lys Ala Ala Ser
    50                  55                  60

Glu Glu Met Asp Lys Ala Val Ala Ala Val Gln Gln Ala Tyr Leu Ala
65                  70                  75                  80

Tyr Gln Gln Ala Thr Asp Lys Ala Ala Lys Asp Ala Ala Asp Lys Met
                85                  90                  95

Ile Asp Glu Ala Lys Lys Arg Glu Glu Glu Ala Lys Thr Lys Phe Asn
            100                 105                 110

Thr Val Arg Ala Met Val Val Pro Glu Pro Glu Gln Leu Ala Glu Thr
        115                 120                 125

Lys Lys Lys Ser Glu Glu Ala Lys Gln Lys Ala Pro Glu Leu Thr Lys
    130                 135                 140

Lys Leu Glu Glu Ala Lys Ala Lys Leu Glu Glu Ala Glu Lys Lys Ala
145                 150                 155                 160

Thr Glu Ala Lys Gln Lys Val Asp Ala Glu Glu Val Ala Pro Gln Ala
                165                 170                 175

Lys Ile Ala Glu Leu Glu Asn Gln Val His Arg Leu Glu Gln Glu Leu
            180                 185                 190

Lys Glu Ile Asp Glu Ser Glu Ser Glu Asp Tyr Ala Lys Glu Gly Phe
        195                 200                 205

Arg Ala Pro Leu Gln Ser Lys Leu Asp Ala Lys Lys Ala Lys Leu Ser
    210                 215                 220

Lys Leu Glu Glu Leu Ser Asp Lys Ile Asp Glu Leu Asp Ala Glu Ile
225                 230                 235                 240

Ala Lys Leu Glu Asp Gln Leu Lys Ala Ala Glu Glu Asn Asn Asn Val
                245                 250                 255

Glu Asp Tyr Phe Lys Glu Gly Leu Glu Lys Thr Ile Ala Ala Lys Lys
            260                 265                 270

Ala Glu Leu Glu Lys Thr Glu Ala Asp Leu Lys Lys Ala Val Asn Glu
        275                 280                 285
```

<210> SEQ ID NO 3
<211> LENGTH: 75
<212> TYPE: PRT
<213> ORGANISM: Streptococcus pneumoniae EF3296

<400> SEQUENCE: 3

```
Leu Ala Lys Lys Gln Thr Glu Leu Glu Lys Leu Leu Asp Ser Leu Asp
1               5                   10                  15

Pro Glu Gly Lys Thr Gln Asp Glu Leu Asp Lys Glu Ala Glu Glu Ala
            20                  25                  30

Glu Leu Asp Lys Lys Ala Asp Glu Leu Gln Asn Lys Val Ala Asp Leu
        35                  40                  45

Glu Lys Glu Ile Ser Asn Leu Glu Ile Leu Leu Gly Gly Ala Asp Ser
    50                  55                  60

Glu Asp Asp Thr Ala Ala Leu Gln Asn Lys Leu
65                  70                  75
```

```
<210> SEQ ID NO 4
<211> LENGTH: 378
<212> TYPE: PRT
<213> ORGANISM: Artificial sequence
<220> FEATURE:
<223> OTHER INFORMATION: synthetic construct

<400> SEQUENCE: 4

Glu Glu Ser Pro Val Ala Ser Gln Ser Lys Ala Glu Lys Asp Tyr Asp
1               5                   10                  15

Ala Ala Lys Lys Asp Ala Lys Asn Ala Lys Lys Ala Val Glu Asp Ala
            20                  25                  30

Gln Lys Ala Leu Asp Asp Ala Lys Ala Ala Gln Lys Lys Tyr Asp Glu
        35                  40                  45

Asp Gln Lys Lys Thr Glu Glu Lys Ala Ala Leu Glu Lys Ala Ala Ser
    50                  55                  60

Glu Glu Met Asp Lys Ala Val Ala Ala Val Gln Gln Ala Tyr Leu Ala
65                  70                  75                  80

Tyr Gln Gln Ala Thr Asp Lys Ala Ala Lys Asp Ala Ala Asp Lys Met
                85                  90                  95

Ile Asp Glu Ala Lys Lys Arg Glu Glu Glu Ala Lys Thr Lys Phe Asn
            100                 105                 110

Thr Val Arg Ala Met Val Val Pro Glu Pro Glu Gln Leu Ala Glu Thr
        115                 120                 125

Lys Lys Lys Ser Glu Glu Ala Lys Gln Lys Ala Pro Glu Leu Thr Lys
    130                 135                 140

Lys Leu Glu Glu Ala Lys Ala Lys Leu Glu Glu Ala Glu Lys Lys Ala
145                 150                 155                 160

Thr Glu Ala Lys Gln Lys Val Asp Ala Glu Glu Val Ala Pro Gln Ala
                165                 170                 175

Lys Ile Ala Glu Leu Glu Asn Gln Val His Arg Leu Glu Gln Glu Leu
            180                 185                 190

Lys Glu Ile Asp Glu Ser Glu Ser Glu Asp Tyr Ala Lys Glu Gly Phe
        195                 200                 205

Arg Ala Pro Leu Gln Ser Lys Leu Asp Ala Lys Lys Ala Lys Leu Ser
    210                 215                 220

Lys Leu Glu Glu Leu Ser Asp Lys Ile Asp Glu Leu Asp Ala Glu Ile
225                 230                 235                 240

Ala Lys Leu Glu Asp Gln Leu Lys Ala Ala Glu Glu Asn Asn Asn Val
                245                 250                 255

Glu Asp Tyr Phe Lys Glu Gly Leu Glu Lys Thr Ile Ala Ala Lys Lys
            260                 265                 270

Ala Glu Leu Glu Lys Thr Glu Ala Asp Leu Lys Lys Ala Val Asn Glu
        275                 280                 285

Gly Gly Gly Gly Ser Gly Gly Gly Gly Ser Gly Gly Gly Gly Ser Leu
    290                 295                 300

Ala Lys Lys Gln Thr Glu Leu Glu Lys Leu Leu Asp Ser Leu Asp Pro
305                 310                 315                 320

Glu Gly Lys Thr Gln Asp Glu Leu Asp Lys Glu Ala Glu Glu Ala Glu
                325                 330                 335

Leu Asp Lys Lys Ala Asp Glu Leu Gln Asn Lys Val Ala Asp Leu Glu
            340                 345                 350
```

```
Lys Glu Ile Ser Asn Leu Glu Ile Leu Leu Gly Gly Ala Asp Ser Glu
        355                 360                 365

Asp Asp Thr Ala Ala Leu Gln Asn Lys Leu
    370                 375


<210> SEQ ID NO 5
<211> LENGTH: 683
<212> TYPE: PRT
<213> ORGANISM: Artificial sequence
<220> FEATURE:
<223> OTHER INFORMATION: synthetic construct

<400> SEQUENCE: 5

Cys Ala Ser Gly Lys Lys Asp Thr Thr Ser Gly Gln Lys Leu Lys Val
1               5                   10                  15

Val Ala Thr Asn Ser Ile Ile Ala Asp Ile Thr Lys Asn Ile Ala Gly
            20                  25                  30

Asp Lys Ile Asp Leu His Ser Ile Val Pro Ile Gly Gln Asp Pro His
        35                  40                  45

Glu Tyr Glu Pro Leu Pro Glu Asp Val Lys Lys Thr Ser Glu Ala Asp
    50                  55                  60

Leu Ile Phe Tyr Asn Gly Ile Asn Leu Glu Thr Gly Gly Asn Ala Trp
65                  70                  75                  80

Phe Thr Lys Leu Val Glu Asn Ala Lys Lys Thr Glu Asn Lys Asp Tyr
                85                  90                  95

Phe Ala Val Ser Asp Gly Val Asp Val Ile Tyr Leu Glu Gly Gln Asn
            100                 105                 110

Glu Lys Gly Lys Glu Asp Pro His Ala Trp Leu Asn Leu Glu Asn Gly
        115                 120                 125

Ile Ile Phe Ala Lys Asn Ile Ala Lys Gln Leu Ser Ala Lys Asp Pro
    130                 135                 140

Asn Asn Lys Glu Phe Tyr Glu Lys Asn Leu Lys Glu Tyr Thr Asp Lys
145                 150                 155                 160

Leu Asp Lys Leu Asp Lys Glu Ser Lys Asp Lys Phe Asn Lys Ile Pro
                165                 170                 175

Ala Glu Lys Lys Leu Ile Val Thr Ser Glu Gly Ala Phe Lys Tyr Phe
            180                 185                 190

Ser Lys Ala Tyr Gly Val Pro Ser Ala Tyr Ile Trp Glu Ile Asn Thr
        195                 200                 205

Glu Glu Glu Gly Thr Pro Glu Gln Ile Lys Thr Leu Val Glu Lys Leu
    210                 215                 220

Arg Gln Thr Lys Val Pro Ser Leu Phe Val Glu Ser Ser Val Asp Asp
225                 230                 235                 240

Arg Pro Met Lys Thr Val Ser Gln Asp Thr Asn Ile Pro Ile Tyr Ala
                245                 250                 255

Gln Ile Phe Thr Asp Ser Ile Ala Glu Gln Gly Lys Glu Gly Asp Ser
            260                 265                 270

Tyr Tyr Ser Met Met Lys Tyr Asn Leu Asp Lys Ile Ala Glu Gly Leu
        275                 280                 285

Ala Lys Gly Gly Gly Gly Ser Gly Gly Gly Gly Ser Gly Gly Gly Gly
    290                 295                 300

Ser Glu Glu Ser Pro Val Ala Ser Gln Ser Lys Ala Glu Lys Asp Tyr
305                 310                 315                 320

Asp Ala Ala Lys Lys Asp Ala Lys Asn Ala Lys Lys Ala Val Glu Asp
                325                 330                 335
```

```
Ala Gln Lys Ala Leu Asp Asp Ala Lys Ala Ala Gln Lys Lys Tyr Asp
            340                 345                 350

Glu Asp Gln Lys Lys Thr Glu Glu Lys Ala Ala Leu Glu Lys Ala Ala
        355                 360                 365

Ser Glu Glu Met Asp Lys Ala Val Ala Ala Val Gln Gln Ala Tyr Leu
    370                 375                 380

Ala Tyr Gln Gln Ala Thr Asp Lys Ala Ala Lys Asp Ala Ala Asp Lys
385                 390                 395                 400

Met Ile Asp Glu Ala Lys Lys Arg Glu Glu Glu Ala Lys Thr Lys Phe
                405                 410                 415

Asn Thr Val Arg Ala Met Val Val Pro Glu Pro Glu Gln Leu Ala Glu
            420                 425                 430

Thr Lys Lys Lys Ser Glu Glu Ala Lys Gln Lys Ala Pro Glu Leu Thr
        435                 440                 445

Lys Lys Leu Glu Glu Ala Lys Ala Lys Leu Glu Glu Ala Glu Lys Lys
    450                 455                 460

Ala Thr Glu Ala Lys Gln Lys Val Asp Ala Glu Glu Val Ala Pro Gln
465                 470                 475                 480

Ala Lys Ile Ala Glu Leu Glu Asn Gln Val His Arg Leu Glu Gln Glu
                485                 490                 495

Leu Lys Glu Ile Asp Glu Ser Glu Ser Glu Asp Tyr Ala Lys Glu Gly
            500                 505                 510

Phe Arg Ala Pro Leu Gln Ser Lys Leu Asp Ala Lys Lys Ala Lys Leu
        515                 520                 525

Ser Lys Leu Glu Glu Leu Ser Asp Lys Ile Asp Glu Leu Asp Ala Glu
    530                 535                 540

Ile Ala Lys Leu Glu Asp Gln Leu Lys Ala Ala Glu Glu Asn Asn Asn
545                 550                 555                 560

Val Glu Asp Tyr Phe Lys Glu Gly Leu Glu Lys Thr Ile Ala Ala Lys
                565                 570                 575

Lys Ala Glu Leu Glu Lys Thr Glu Ala Asp Leu Lys Lys Ala Val Asn
            580                 585                 590

Glu Gly Gly Gly Gly Ser Gly Gly Gly Gly Ser Gly Gly Gly Gly Ser
        595                 600                 605

Leu Ala Lys Lys Gln Thr Glu Leu Glu Lys Leu Leu Asp Ser Leu Asp
    610                 615                 620

Pro Glu Gly Lys Thr Gln Asp Glu Leu Asp Lys Glu Ala Glu Glu Ala
625                 630                 635                 640

Glu Leu Asp Lys Lys Ala Asp Glu Leu Gln Asn Lys Val Ala Asp Leu
                645                 650                 655

Glu Lys Glu Ile Ser Asn Leu Glu Ile Leu Leu Gly Gly Ala Asp Ser
            660                 665                 670

Glu Asp Asp Thr Ala Ala Leu Gln Asn Lys Leu
        675                 680
```

<210> SEQ ID NO 6
<211> LENGTH: 2049
<212> TYPE: DNA
<213> ORGANISM: Artificial sequence
<220> FEATURE:
<223> OTHER INFORMATION: synthetic construct

<400> SEQUENCE: 6

```
tgcgcgtctg gtaaaaaaga taccacctct ggtcagaaac tgaaagttgt tgcgaccaac      60

tctatcatcg cggatatcac caaaaacatc gcgggtgata aaatcgatct gcactctatc     120
```

```
gttccgatcg gtcaggaccc gcacgaatac gaaccgctgc cggaagatgt taaaaaaacc    180
tctgaagcgg atctgatctt ctacaacggt atcaacctgg aaaccggtgg taacgcgtgg    240
ttcaccaaac tggttgaaaa cgcgaaaaaa accgaaaaca aagattactt cgcggtttct    300
gatggtgttg atgttatcta cctggaaggt cagaacgaaa aaggtaaaga agatccgcac    360
gcgtggctga acctggaaaa cggtatcatc ttcgcgaaaa acatcgcgaa acagctgtct    420
gcgaaagatc cgaacaacaa agaattttac gaaaaaaacc tgaaagaata caccgataaa    480
ctggataaac tggataaaga atctaaagat aaattcaaca aaatcccggc ggaaaaaaaa    540
ctgatcgtta cctctgaagg tgcgttcaaa tacttctcta aagcgtacgg tgttccgtct    600
gcgtacatct gggaaatcaa caccgaagaa gaaggtaccc cggaacagat caaaaccctg    660
gttgaaaaac tgcgtcagac caaagttccg tctctgttcg ttgaatcttc tgttgatgat    720
cgtccgatga aaaccgtttc tcaggatacc aacatcccga tctacgcgca gatcttcacc    780
gattctatcg cggaacaggg taaagaaggt gattcttact actctatgat gaaatacaac    840
ctggataaaa tcgcggaagg tctggcgaaa ggtggtggtg gttctggtgg tggtggttct    900
ggtggtggtg gttctgaaga atctccggtt gcgtctcagt ctaaagcgga aaaagattat    960
gatgcggcga aaaaagatgc gaaaaacgcg aaaaaagcgg ttgaagatgc gcagaaagcg   1020
ctggatgatg cgaaagcggc gcagaaaaaa tatgatgaag atcagaaaaa aaccgaagaa   1080
aaagcggcgc tggaaaaagc ggcgtctgaa gaaatggata aagcggttgc ggcggttcag   1140
caggcgtatc tggcgtatca gcaggcgacc gataaagcgg cgaaagatgc ggcggataaa   1200
atgatcgatg aagcgaaaaa acgtgaagaa gaagcgaaaa ccaaattcaa caccgttcgt   1260
gcgatggttg ttccggaacc ggaacagctg gcggaaacca aaaaaaaatc tgaagaagcg   1320
aaacagaaag cgccggaact gaccaaaaaa ctggaagaag cgaaagcgaa actggaagaa   1380
gcggaaaaaa aagcgaccga agcgaaacag aaagttgatg cggaagaagt tgcgccgcag   1440
gcgaaaatcg cggaactgga aaaccaggtt caccgtctgg aacaggaact gaaagaaatc   1500
gatgaatctg aatctgaaga ttatgcgaaa gaaggtttcc gtgcgccgct gcagtctaaa   1560
ctggatgcga aaaaagcgaa actgtctaaa ctggaagaac tgtctgataa aatcgatgaa   1620
ctggatgcgg aaatcgcgaa actggaagat cagctgaaag cggcggaaga aaacaacaac   1680
gttgaagatt atttcaaaga aggtctggaa aaaaccatcg cggcgaaaaa agcggaactg   1740
gaaaaaaccg aagcggatct gaaaaaagcg gttaacgaag gtggtggtgg ttctggtggt   1800
ggtggttctg gtggtggtgg ttctctggcg aaaaaacaga ccgaactgga aaaactgctg   1860
gattctctgg acccggaagg taaaacccag gatgaactgg ataaagaagc ggaagaagcg   1920
gaactggata aaaaagcgga tgaactgcag aacaaagttg cggatctgga aaaagaaatc   1980
tctaacctgg aaatcctgct gggtggtgcg gattctgaag atgataccgc ggcgctgcag   2040
aacaaactg                                                           2049
```

<210> SEQ ID NO 7
<211> LENGTH: 2079
<212> TYPE: DNA
<213> ORGANISM: Artificial sequence
<220> FEATURE:
<223> OTHER INFORMATION: synthetic construct

<400> SEQUENCE: 7

```
catatgcacc accaccacca ccactgcgcg tctggtaaaa aagataccac ctctggtcag     60
aaactgaaag ttgttgcgac caactctatc atcgcggata tcaccaaaaa catcgcgggt    120
```

-continued

```
gataaaatcg atctgcactc tatcgttccg atcggtcagg acccgcacga atacgaaccg    180

ctgccggaag atgttaaaaa aacctctgaa gcggatctga tcttctacaa cggtatcaac    240

ctggaaaccg gtggtaacgc gtggttcacc aaactggttg aaaacgcgaa aaaaaccgaa    300

aacaaagatt acttcgcggt ttctgatggt gttgatgtta tctacctgga aggtcagaac    360

gaaaaaggta aagaagatcc gcacgcgtgg ctgaacctgg aaaacggtat catcttcgcg    420

aaaaacatcg cgaaacagct gtctgcgaaa gatccgaaca acaaagaatt ttacgaaaaa    480

aacctgaaag aatacaccga taaactggat aaactggata aagaatctaa agataaattc    540

aacaaaatcc cggcggaaaa aaaactgatc gttacctctg aaggtgcgtt caaatacttc    600

tctaaagcgt acggtgttcc gtctgcgtac atctgggaaa tcaacaccga agaagaaggt    660

accccggaac agatcaaaac cctggttgaa aaactgcgtc agaccaaagt tccgtctctg    720

ttcgttgaat cttctgttga tgatcgtccg atgaaaaccg tttctcagga taccaacatc    780

ccgatctacg cgcagatctt caccgattct atcgcggaac agggtaaaga aggtgattct    840

tactactcta tgatgaaata caacctggat aaaatcgcgg aaggtctggc gaaaggtggt    900

ggtggttctg gtggtggtgg ttctggtggt ggtggttctg aagaatctcc ggttgcgtct    960

cagtctaaag cggaaaaaga ttatgatgcg gcgaaaaaag atgcgaaaaa cgcgaaaaaa   1020

gcggttgaag atgcgcagaa agcgctggat gatgcgaaag cggcgcagaa aaaatatgat   1080

gaagatcaga aaaaaaccga agaaaaagcg gcgctggaaa aagcggcgtc tgaagaaatg   1140

gataaagcgg ttgcggcggt tcagcaggcg tatctggcgt atcagcaggc gaccgataaa   1200

gcggcgaaag atgcggcgga taaaatgatc gatgaagcga aaaaacgtga agaagaagcg   1260

aaaaccaaat tcaacaccgt tcgtgcgatg gttgttccgg aaccggaaca gctggcggaa   1320

accaaaaaaa aatctgaaga agcgaaacag aaagcgccgg aactgaccaa aaaactggaa   1380

gaagcgaaag cgaaactgga agaagcggaa aaaaaagcga ccgaagcgaa acagaaagtt   1440

gatgcggaag aagttgcgcc gcaggcgaaa atcgcggaac tggaaaacca ggttcaccgt   1500

ctggaacagg aactgaaaga aatcgatgaa tctgaatctg aagattatgc gaaagaaggt   1560

ttccgtgcgc cgctgcagtc taaactggat gcgaaaaaag cgaaactgtc taaactggaa   1620

gaactgtctg ataaaatcga tgaactggat gcggaaatcg cgaaactgga agatcagctg   1680

aaagcggcgg aagaaaacaa caacgttgaa gattatttca aagaaggtct ggaaaaaacc   1740

atcgcggcga aaaaagcgga actggaaaaa accgaagcgg atctgaaaaa agcggttaac   1800

gaaggtggtg gtggttctgg tggtggtggt tctggtggtg gtggttctct ggcgaaaaaa   1860

cagaccgaac tggaaaaact gctggattct ctggacccgg aaggtaaaac ccaggatgaa   1920

ctggataaag aagcggaaga agcggaactg gataaaaaag cggatgaact gcagaacaaa   1980

gttgcggatc tggaaaaaga aatctctaac ctggaaatcc tgctgggtgg tgcggattct   2040

gaagatgata ccgcggcgct gcagaacaaa ctgctcgag                          2079


<210> SEQ ID NO 8
<211> LENGTH: 419
<212> TYPE: PRT
<213> ORGANISM: Streptococcus pneumoniae EF5668

<400> SEQUENCE: 8

Glu Glu Ala Pro Val Ala Asn Gln Ser Lys Ala Glu Lys Asp Tyr Asp
1               5                   10                  15

Ala Ala Val Lys Lys Ser Glu Ala Ala Lys Lys Asp Tyr Glu Thr Ala
            20                  25                  30
```

```
Lys Lys Lys Ala Glu Asp Ala Gln Lys Lys Tyr Asp Glu Asp Gln Lys
        35                  40                  45

Lys Thr Glu Ala Lys Ala Glu Lys Glu Arg Lys Ala Ser Glu Lys Ile
    50                  55                  60

Ala Glu Ala Thr Lys Glu Val Gln Gln Ala Tyr Leu Ala Tyr Leu Gln
65                  70                  75                  80

Ala Ser Asn Glu Ser Gln Arg Lys Glu Ala Asp Lys Lys Ile Lys Glu
                85                  90                  95

Ala Thr Gln Arg Lys Asp Glu Ala Glu Ala Ala Phe Ala Thr Ile Arg
            100                 105                 110

Thr Thr Ile Val Val Pro Glu Pro Ser Glu Leu Ala Glu Thr Lys Lys
        115                 120                 125

Lys Ala Glu Glu Ala Thr Lys Glu Ala Glu Val Ala Lys Lys Lys Ser
    130                 135                 140

Glu Glu Ala Ala Lys Glu Val Glu Val Glu Lys Asn Lys Ile Leu Glu
145                 150                 155                 160

Gln Asp Ala Glu Asn Glu Lys Lys Ile Asp Val Leu Gln Asn Lys Val
                165                 170                 175

Ala Asp Leu Glu Lys Gly Ile Ala Pro Tyr Gln Asn Glu Val Ala Glu
            180                 185                 190

Leu Asn Lys Glu Ile Ala Arg Leu Gln Ser Asp Leu Lys Asp Ala Glu
        195                 200                 205

Glu Asn Asn Val Glu Asp Tyr Ile Lys Glu Gly Leu Glu Gln Ala Ile
    210                 215                 220

Thr Asn Lys Lys Ala Glu Leu Ala Thr Thr Gln Gln Asn Ile Asp Lys
225                 230                 235                 240

Thr Gln Lys Asp Leu Glu Asp Ala Glu Leu Glu Leu Glu Lys Val Leu
                245                 250                 255

Ala Thr Leu Asp Pro Glu Gly Lys Thr Gln Asp Glu Leu Asp Lys Glu
            260                 265                 270

Ala Ala Glu Ala Glu Leu Asn Glu Lys Val Glu Ala Leu Gln Asn Gln
        275                 280                 285

Val Ala Glu Leu Glu Glu Glu Leu Ser Lys Leu Glu Asp Asn Leu Lys
    290                 295                 300

Asp Ala Glu Thr Asn Asn Val Glu Asp Tyr Ile Lys Glu Gly Leu Glu
305                 310                 315                 320

Glu Ala Ile Ala Thr Lys Lys Ala Glu Leu Glu Lys Thr Gln Lys Glu
                325                 330                 335

Leu Asp Ala Ala Leu Asn Glu Leu Gly Pro Asp Gly Asp Glu Glu Glu
            340                 345                 350

Thr Pro Ala Pro Ala Pro Gln Pro Glu Lys Pro Ala Glu Glu Pro Glu
        355                 360                 365

Asn Pro Ala Pro Ala Pro Lys Pro Glu Lys Ser Ala Asp Gln Gln Ala
    370                 375                 380

Glu Glu Asp Tyr Ala Arg Arg Ser Glu Glu Glu Tyr Asn Arg Leu Thr
385                 390                 395                 400

Gln Gln Gln Pro Pro Lys Ala Glu Lys Pro Ala Pro Ala Pro Gln Pro
                405                 410                 415

Glu Gln Pro
```

<210> SEQ ID NO 9
<211> LENGTH: 1257
<212> TYPE: DNA
<213> ORGANISM: Artificial sequence

```
<220> FEATURE:
<223> OTHER INFORMATION: synthetic construct

<400> SEQUENCE: 9

gaagaagcgc cggttgcgaa ccagtctaaa gcggaaaaag attatgatgc ggcggttaaa      60

aaatctgaag cggcgaaaaa agattatgaa accgcgaaaa aaaaagcgga agatgcgcag     120

aaaaaatatg atgaagatca gaaaaaaacc gaagcgaaag cggaaaaaga acgtaaagcg     180

tctgaaaaaa tcgcggaagc gaccaaagaa gttcagcagg cgtatctggc gtatctgcag     240

gcgtctaacg aatctcagcg taaagaagcg gataaaaaaa tcaaagaagc gacccagcgt     300

aaagatgaag cggaagcggc gttcgcgacc atccgtacca ccatcgttgt tccggaaccg     360

tctgaactgg cggaaaccaa aaaaaaagcg gaagaagcga ccaaagaagc ggaagttgcg     420

aaaaaaaaat ctgaagaagc ggcgaaagaa gttgaagttg aaaaaaacaa aatcctggaa     480

caggatgcgg aaaacgaaaa aaaaatcgat gttctgcaga acaaagttgc ggatctggaa     540

aaaggtatcg cgccgtatca gaacgaagtt gcggaactga acaaagaaat cgcgcgtctg     600

cagtctgatc tgaaagatgc ggaagaaaac aacgttgaag attatatcaa agaaggtctg     660

gaacaggcga tcaccaacaa aaaagcggaa ctggcgacca cccagcagaa catcgataaa     720

acccagaaag atctggaaga tgcggaactg gaactggaaa aagttctggc gaccctggac     780

ccggaaggta aaacccagga tgaactggat aaagaagcgg cggaagcgga actgaacgaa     840

aaagttgaag cgctgcagaa ccaggttgcg gaactggaag aagaactgtc taaactggaa     900

gataacctga aagatgcgga aaccaacaac gttgaagatt atatcaaaga aggtctggaa     960

gaagcgatcg cgaccaaaaa agcggaactg gaaaaaaccc agaaagaact ggatgcggcg    1020

ctgaacgaac tgggtccgga tggtgatgaa gaagaaaccc cggcgccggc gccgcagccg    1080

gaaaaaccgg cggaagaacc ggaaaacccg gcgccggcgc cgaaaccgga aaaatctgcg    1140

gatcagcagg cggaagaaga ttatgcgcgt cgttctgaag aagaatataa ccgtctgacc    1200

cagcagcagc cgccgaaagc ggaaaaaccg gcgccggcgc cgcagccgga acagccg       1257


<210> SEQ ID NO 10
<211> LENGTH: 1269
<212> TYPE: DNA
<213> ORGANISM: Artificial sequence
<220> FEATURE:
<223> OTHER INFORMATION: synthetic construct

<400> SEQUENCE: 10

catatggaag aagcgccggt tgcgaaccag tctaaagcgg aaaaagatta tgatgcggcg      60

gttaaaaaat ctgaagcggc gaaaaaagat tatgaaaccg cgaaaaaaaa agcggaagat     120

gcgcagaaaa aatatgatga agatcagaaa aaaaccgaag cgaaagcgga aaaagaacgt     180

aaagcgtctg aaaaaatcgc ggaagcgacc aaagaagttc agcaggcgta tctggcgtat     240

ctgcaggcgt ctaacgaatc tcagcgtaaa gaagcggata aaaaaatcaa agaagcgacc     300

cagcgtaaag atgaagcgga agcggcgttc gcgaccatcc gtaccaccat cgttgttccg     360

gaaccgtctg aactggcgga aaccaaaaaa aaagcggaag aagcgaccaa agaagcggaa     420

gttgcgaaaa aaaaatctga agaagcggcg aaagaagttg aagttgaaaa aaacaaaatc     480

ctggaacagg atgcggaaaa cgaaaaaaaa atcgatgttc tgcagaacaa agttgcggat     540

ctggaaaaag gtatcgcgcc gtatcagaac gaagttgcgg aactgaacaa agaaatcgcg     600

cgtctgcagt ctgatctgaa agatgcggaa gaaaacaacg ttgaagatta tatcaaagaa     660
```

ggtctggaac aggcgatcac caacaaaaaa gcggaactgg cgaccaccca gcagaacatc 720
gataaaaccc agaaagatct ggaagatgcg gaactggaac tggaaaaagt tctggcgacc 780
ctggacccgg aaggtaaaac ccaggatgaa ctggataaag aagcggcgga agcggaactg 840
aacgaaaaag ttgaagcgct gcagaaccag gttgcggaac tggaagaaga actgtctaaa 900
ctggaagata acctgaaaga tgcggaaacc aacaacgttg aagattatat caaagaaggt 960
ctggaagaag cgatcgcgac caaaaaagcg gaactggaaa aaacccagaa agaactggat 1020
gcggcgctga acgaactggg tccggatggt gatgaagaag aaaccccggc gccggcgccg 1080
cagccggaaa aaccggcgga agaaccggaa aacccggcgc cggcgccgaa accggaaaaa 1140
tctgcggatc agcaggcgga agaagattat gcgcgtcgtt ctgaagaaga atataaccgt 1200
ctgacccagc agcagccgcc gaaagcggaa aaaccggcgc cggcgccgca gccggaacag 1260
ccgctcgag 1269

<210> SEQ ID NO 11
<211> LENGTH: 882
<212> TYPE: DNA
<213> ORGANISM: Artificial sequence
<220> FEATURE:
<223> OTHER INFORMATION: synthetic construct

<400> SEQUENCE: 11
catatgtgcg cgtctggtaa aaaagatacc acctctggtc agaaactgaa agttgttgcg 60
accaactcta tcatcgcgga tatcaccaaa aacatcgcgg gtgataaaat cgatctgcac 120
tctatcgttc cgatcggtca ggacccgcac gaatacgaac cgctgccgga agatgttaaa 180
aaaacctctg aagcggatct gatcttctac aacggtatca acctggaaac cggtggtaac 240
gcgtggttca ccaaactggt tgaaaacgcg aaaaaaaccg aaaacaaaga ttacttcgcg 300
gtttctgatg gtgttgatgt tatctacctg gaaggtcaga acgaaaaagg taaagaagat 360
ccgcacgcgt ggctgaacct ggaaaacggt atcatcttcg cgaaaaacat cgcgaaacag 420
ctgtctgcga aagatccgaa caacaaagaa ttttacgaaa aaaacctgaa agaatacacc 480
gataaactgg ataaactgga taaagaatct aaagataaat tcaacaaaat cccggcggaa 540
aaaaaactga tcgttacctc tgaaggtgcg ttcaaatact tctctaaagc gtacggtgtt 600
ccgtctgcgt acatctggga aatcaacacc gaagaagaag gtaccccgga acagatcaaa 660
accctggttg aaaaactgcg tcagaccaaa gttccgtctc tgttcgttga atcttctgtt 720
gatgatcgtc cgatgaaaac cgtttctcag gataccaaca tcccgatcta cgcgcagatc 780
ttcaccgatt ctatcgcgga acagggtaaa gaaggtgatt cttactactc tatgatgaaa 840
tacaacctgg ataaaatcgc ggaaggtctg gcgaaactcg ag 882

<210> SEQ ID NO 12
<211> LENGTH: 1146
<212> TYPE: DNA
<213> ORGANISM: Artificial sequence
<220> FEATURE:
<223> OTHER INFORMATION: synthetic construct

<400> SEQUENCE: 12
catatggaag aatctccggt tgcgtctcag tctaaagcgg aaaaagatta tgatgcggcg 60
aaaaaagatg cgaaaaacgc gaaaaaagcg gttgaagatg cgcagaaagc gctggatgat 120
gcgaaagcgg cgcagaaaaa atatgatgaa gatcagaaaa aaaccgaaga aaaagcggcg 180
ctggaaaaag cggcgtctga agaaatggat aaagcggttg cggcggttca gcaggcgtat 240

```
ctggcgtatc agcaggcgac cgataaagcg gcgaaagatg cggcggataa aatgatcgat    300

gaagcgaaaa aacgtgaaga agaagcgaaa accaaattca acaccgttcg tgcgatggtt    360

gttccggaac cggaacagct ggcggaaacc aaaaaaaaat ctgaagaagc gaaacagaaa    420

gcgccggaac tgaccaaaaa actggaagaa gcgaaagcga aactggaaga agcggaaaaa    480

aaagcgaccg aagcgaaaca gaaagttgat gcggaagaag ttgcgccgca ggcgaaaatc    540

gcggaactgg aaaaccaggt tcaccgtctg gaacaggaac tgaaagaaat cgatgaatct    600

gaatctgaag attatgcgaa agaaggtttc cgtgcgccgc tgcagtctaa actggatgcg    660

aaaaaagcga aactgtctaa actggaagaa ctgtctgata aaatcgatga actggatgcg    720

gaaatcgcga aactggaaga tcagctgaaa gcggcggaag aaaacaacaa cgttgaagat    780

tatttcaaag aaggtctgga aaaaaccatc gcggcgaaaa aagcggaact ggaaaaaacc    840

gaagcggatc tgaaaaaagc ggttaacgaa ggtggtggtg gttctggtgg tggtggttct    900

ggtggtggtg gttctctggc gaaaaaacag accgaactgg aaaaactgct ggattctctg    960

gacccggaag gtaaaaccca ggatgaactg gataaagaag cggaagaagc ggaactggat   1020

aaaaaagcgg atgaactgca gaacaaagtt gcggatctgg aaaaagaaat ctctaacctg   1080

gaaatcctgc tgggtggtgc ggattctgaa gatgataccg cggcgctgca gaacaaactg   1140

ctcgag                                                              1146
```

<210> SEQ ID NO 13
<211> LENGTH: 28
<212> TYPE: DNA
<213> ORGANISM: Artificial sequence
<220> FEATURE:
<223> OTHER INFORMATION: synthetic construct

<400> SEQUENCE: 13

```
catatgtgcg cgtctggtaa aaaagata                                        28
```

<210> SEQ ID NO 14
<211> LENGTH: 27
<212> TYPE: DNA
<213> ORGANISM: Artificial sequence
<220> FEATURE:
<223> OTHER INFORMATION: synthetic construct

<400> SEQUENCE: 14

```
ctcgagtttc gccagacctt ccgcgat                                         27
```

<210> SEQ ID NO 15
<211> LENGTH: 27
<212> TYPE: DNA
<213> ORGANISM: Artificial sequence
<220> FEATURE:
<223> OTHER INFORMATION: synthetic construct

<400> SEQUENCE: 15

```
catatggaag aatctccggt tgcgtct                                         27
```

<210> SEQ ID NO 16
<211> LENGTH: 27
<212> TYPE: DNA
<213> ORGANISM: Artificial sequence
<220> FEATURE:
<223> OTHER INFORMATION: synthetic construct -continued

<400> SEQUENCE: 16

```
ctcgagcagt ttgttctgca gcgccgc                                          27
```